United States Patent
Johnson et al.

(10) Patent No.: US 8,410,466 B2
(45) Date of Patent: *Apr. 2, 2013

(54) NON-CONTACT COMPONENT INSPECTION SYSTEM

(75) Inventors: Stanley P. Johnson, Simsbury, CT (US); Lawrence J. Zagorsky, Lincoln, RI (US)

(73) Assignee: Quest Metrology Group, LLC, Kent, WA (US)

( * ) Notice: Subject to any disclaimer, the term of this patent is extended or adjusted under 35 U.S.C. 154(b) by 417 days.

This patent is subject to a terminal disclaimer.

(21) Appl. No.: 12/798,586

(22) Filed: Apr. 7, 2010

(65) Prior Publication Data

US 2010/0270484 A1    Oct. 28, 2010

Related U.S. Application Data

(63) Continuation-in-part of application No. 11/391,521, filed on Mar. 27, 2006, now Pat. No. 7,745,805, which is a continuation-in-part of application No. 10/460,941, filed on Jun. 13, 2003, now Pat. No. 7,227,163.

(60) Provisional application No. 60/389,357, filed on Jun. 17, 2002.

(51) Int. Cl.
*G01N 21/86* (2006.01)
*G01B 11/24* (2006.01)

(52) U.S. Cl. .................. 250/559.42; 356/613

(58) Field of Classification Search ............ 250/559.12–559.15, 559.24, 559.42; 356/237.1, 613, 356/638–640

See application file for complete search history.

(56) References Cited

U.S. PATENT DOCUMENTS

| | | | |
|---|---|---|---|
| 3,009,253 A | 11/1961 | Swanson et al. |
| 3,941,484 A | 3/1976 | Dreyfus |
| 4,021,119 A | 5/1977 | Stauffer |
| 4,062,633 A | 12/1977 | Stapleton et al. |
| 4,576,482 A | 3/1986 | Pryor |
| 4,634,273 A | 1/1987 | Farleman et al. |

(Continued)

OTHER PUBLICATIONS

Mutan, Comparison of Regression Techniques Via Monte Carlo Simulation, Jun. 2004, 33 pages.

(Continued)

*Primary Examiner* — Thanh Luu
(74) *Attorney, Agent, or Firm* — Christensen O'Connor Johnson Kindness PLLC

(57) ABSTRACT

A system and method for measuring the physical characteristics of a component where the system includes an electromagnetic radiation source defining a source optical path, the electromagnetic radiation source being operable to cause electromagnetic radiation to propagate along the source optical path, a sensing device defining a sensor optical path, a system support structure, a base structure, an electromagnetic radiation source mounting structure and a sensing device mounting structure, a positioning device including a positioning device stage, wherein the positioning device stage is movably disposed and a retention mount disposed on the positioning device stage, the retention mount being disposed within the sensor optical path such that when a component is retained within the retention mount, the component blocks at least a portion of the electromagnetic radiation to generate a silhouette, wherein the sensing device generates data responsive to the silhouette.

7 Claims, 29 Drawing Sheets

U.S. PATENT DOCUMENTS

| | | |
|---|---|---|
| 4,644,394 A | 2/1987 | Reeves |
| 4,747,689 A | 5/1988 | Aldred |
| 4,748,332 A | 5/1988 | Kuhne et al. |
| 4,753,532 A | 6/1988 | Aldred |
| 4,871,910 A | 10/1989 | Ueno et al. |
| 4,872,757 A | 10/1989 | Cormack et al. |
| 4,966,460 A * | 10/1990 | Kahley .................. 356/640 |
| 5,150,623 A | 9/1992 | Woods |
| 5,175,595 A | 12/1992 | Fukase |
| 5,278,634 A | 1/1994 | Skunes et al. |
| 5,296,914 A | 3/1994 | Aldred |
| 5,521,707 A | 5/1996 | Castore et al. |
| 5,646,724 A | 7/1997 | Hershline |
| 5,712,706 A | 1/1998 | Castore et al. |
| 5,796,485 A | 8/1998 | Dassler et al. |
| 5,841,542 A | 11/1998 | Milana et al. |
| 5,897,611 A | 4/1999 | Case et al. |
| 5,914,784 A | 6/1999 | Ausschnitt et al. |
| 6,055,329 A | 4/2000 | Mufti |
| 6,064,759 A | 5/2000 | Buckley et al. |
| 6,111,601 A | 8/2000 | Adachi |
| 6,141,106 A | 10/2000 | Blum |
| 6,172,748 B1 | 1/2001 | Sones et al. |
| 6,404,912 B1 | 6/2002 | Lehnen et al. |
| 6,683,995 B2 | 1/2004 | Ford et al. |
| 7,777,209 B2 | 8/2010 | Johnson et al. |
| 2002/0041381 A1 | 4/2002 | Akishiba |
| 2003/0101602 A1 | 6/2003 | Galestien |
| 2004/0150815 A1 | 8/2004 | Sones et al. |
| 2008/0049235 A1 | 2/2008 | Crowther |
| 2008/0151268 A1 | 6/2008 | Archie et al. |
| 2009/0101851 A1 | 4/2009 | Spalding |
| 2009/0179162 A1 | 7/2009 | Johnson |
| 2010/0245845 A1 | 9/2010 | Johnson et al. |
| 2010/0259764 A1 | 10/2010 | Johnson et al. |

OTHER PUBLICATIONS

Gabriel, Least Squares Approximation of Matrices by Additive and Multiplicative Models, Journal of Royal Statistical Society, Series B (Methodological), vol. 40 No. 2, Dec. 1978, 12 pages.

* cited by examiner

A - A

NON-CONTACT COMPONENT INSPECTION SYSTEM

RELATED APPLICATIONS

This application is a Continuation-In-Part of U.S. application Ser. No. 11/391,521 filed Mar. 27, 2006 now U.S. Pat. No. 7,745,805 entitled "A Product Inspection System and a Method for Implementing same that Incorporates a Correction Factor", which is a continuation-in-parts of U.S. application Ser. No. 10/460,941 filed Jun. 13, 2003 now U.S. Pat. No. 7,227,163 entitled "Inspection System and Method", the contents of which are incorporated herein by reference in their entirety. This application claims the benefit of the filing date of U.S. Provisional Patent Application Ser. No. 60/389,357, filed Jun. 17, 2002.

FIELD OF THE INVENTION

This disclosure relates generally to a method and system for inspecting components and more particularly to a method and system for optically inspecting the physical characteristics of externally threaded components, such as thread gages, screws, bolts and other externally threaded components having varied configurations.

BACKGROUND OF THE INVENTION

As society becomes increasingly reliant upon technology, mechanical and electromechanical systems, such as aircraft, automobiles, weapons systems and power systems, are called upon to perform an ever increasing number of functions. One downside to this is that, in some situations, a failure of a single threaded component in the system may cause a catastrophic failure of the entire system possibly resulting in the loss of millions of dollars and hundreds of lives. In an attempt to reduce the probability of a catastrophic systems failure, critical and some non-critical systems are required to satisfy predetermine operating tolerances before they may be used. As such, key threaded components within these systems, i.e. threaded components whose failure may cause a catastrophic system failure such as screws and/or gages, must also satisfy operating tolerances. If a threaded component fails to satisfy these required design tolerances and/or performance specifications, a degradation of system performance and/or a total system failure may occur resulting in damage to the system and/or injury/loss of life to an operator.

One of the current systems used for inspecting the physical characteristics of a threaded component employ an attribute inspection approach that measures the characteristics of the threaded component via a contact measurement technique which does not protect product design limits. This technique uses GO and/or No Go ring gages that are adjusted, or calibrated, to a desired thread measurement via Go and/or No Go setting plugs. Unfortunately, this technique does not ensure the integrity of design limits and because this approach is dependent upon human interaction, this technique has the disadvantage of being time consuming; subjectively inaccurate and unreliably repeatable for tight operating tolerances, thus permitting threaded components having dimensionally non-conforming characteristics to pass inspections. Moreover, there is a considerable wear factor on the measuring instruments, requiring the Go, No Go setting plugs to be inspected and replaced often.

Another approach used for measuring external thread gages utilizes three wires communicated to the gage being measured. The three wires are of a known diameter and are typically disposed between the threads of a component such that the wires protrude from the threads, wherein two wires are disposed on one side of the threaded component and one wire is disposed on the opposing side of the threaded component. The diameter over the wires is then measured via a human inspector. Because the wires are of a known diameter, this allows certain characteristics of the threads to be determined by measuring the width of the wires disposed between the threads. Unfortunately, this approach is also dependent upon human interaction. If the inspector measuring the distance over the wires compresses the wires too much, the wires may become deformed resulting in an inaccurate measurement. Additionally, the surface finish of a threaded component may adversely affect the accuracies of these measurements. Moreover, because the wires are loose and are not held between the threads, the wires may be dropped which may result in the wires becoming contaminated with dirt, the wires being lost or, if someone steps on them, the wires being deformed.

Furthermore, different operators will generate different gage pressures on the wires which may cause erroneous readings. Thus, this approach has the similar disadvantage of being time consuming, subjectively inaccurate and unreliably repeatable for tight operating tolerances, thus also permitting threaded components having dimensionally non-conforming characteristics to pass inspections. Additionally, the reliability and repeatability of this measurement is very poor because an operator must measure angles using an optical projection which is also time consuming, inaccurate and often fails to satisfy current product and gage calibration specifications. As such, the Measurement Uncertainty Factor (MUF) in many situations exceeds the required tolerances and as a result, the required accuracies for complete certification of these methods have thus far been unobtainable.

SUMMARY OF THE INVENTION

An inspection system is provided and includes an electromagnetic radiation source defining a source optical path, the electromagnetic radiation source being operable to cause electromagnetic radiation to propagate along the source optical path; a sensing device defining a sensor optical path, a system support structure, a base structure, a bridge structure, an electromagnetic radiation source mounting structure and a sensing device mounting structure. A positioning device is also provided and includes a positioning device stage, wherein the positioning device stage is movably disposed relative to the positioning device, the sensing device and the electromagnetic radiation source, and wherein the positioning device is non-movably disposed on the base structure and a retention mount non-movably disposed on the positioning device stage, the retention mount being disposed within the sensor optical path such that when a component is retained within the retention mount, the component blocks at least a portion of the electromagnetic radiation to generate a silhouette, wherein the sensing device generates data responsive to the silhouette.

An inspection system, is provided and includes a collimated light source defining a source optical path, the collimated light source being operable to cause a collimated light beam to propagate along the source optical path, a sensing device defining a sensor optical path, a system support structure, a base structure, a bridge structure, a light source mounting structure and a sensing device mounting structure, a positioning device including a positioning device stage, wherein the positioning device stage is movably disposed relative to the positioning device, the sensing device and the collimated light source, and wherein the positioning device is non-movably disposed on the base structure. Also included is a retention mount non-movably disposed on the positioning device stage, the retention mount being disposed within the sensor optical path such that when a component is retained within the retention mount, the component blocks at least a portion of the collimated light beam.

An inspection system is provided and includes a collimated light source defining a source optical path, the collimated light source being operable to cause a collimated light beam to propagate along the source optical path, a sensing device defining a sensor optical path, a system support structure, a base structure, a bridge structure, a light source mounting structure and a sensing device mounting structure; a positioning device including a positioning device stage, wherein the positioning device stage is movably disposed relative to the positioning device, the sensing device and the collimated light source, and wherein the positioning device is non-movably disposed on the base structure and a retention mount non-movably disposed on the positioning device stage, the retention mount being disposed within the sensor optical path such that when a component is retained within the retention mount, the component blocks at least a portion of the collimated light beam.

An inspection system is provided and includes a collimated light source defining a source optical path, wherein the collimated light source is operable to cause a collimated light beam to propagate along the source optical path, a sensing device defining a sensor optical path, a positioning device including a positioning device stage, the positioning device stage movably disposed relative to the sensing device and the collimated light source, a reflecting device, the reflecting device disposed on the positioning device to be within the source optical path to receive the collimated light beam, the reflecting device causing a reflected collimated light beam to propagate along the sensor optical path to the sensing device, wherein the reflected collimated light beam is incident upon an object disposed within the sensor optical path such that a silhouette of the object is generated and incident upon the sensing device, such that the sensing device generates initial data responsive to at least one of the silhouette and the reflected collimated light beam and at least one processing device, wherein the at least one processing device is communicated with the sensing device to receive at least a portion of the initial data, wherein the processing device processes the at least a portion of the initial data responsive to a Correction Factor (CF).

A method for measuring physical characteristics of an object using an inspection system, wherein the inspection system includes a light source defining a source optical path, a sensing device defining a sensor optical path, a reflecting device disposed to communicate the source optical path with the sensor optical path and at least one processing device communicated with the sensing device is provided, wherein the method includes associating the object with the inspection system such that the object is disposed within the sensor optical path, operating the inspection system to cause the light source to emit a source collimated light beam propagating along the source optical path to be at least partially incident upon the reflecting device, reflecting the source collimated light beam via the reflecting device to create a reflected collimated light beam that propagates along the sensor optical path such that the reflected collimated light beam is at least partially incident upon the object to produce a silhouette, wherein at least a portion of the silhouette is incident upon the sensing device to generate initial image data responsive to the silhouette and processing the initial image data responsive to at least one predetermined algorithm to generate resultant image data responsive to at least one of a plurality of physical characteristics of the object.

A method for correcting aberrations in a component silhouette generated by a component inspection system, wherein the component inspection system includes a light source defining a source optical path, a sensing device defining a sensor optical path, a reflecting device disposed to communicate the source optical path with the sensor optical path and at least one processing device communicated with the sensing device is provided, the method includes associating the object with the inspection system such that the object is disposed within the sensor optical path, operating the light source to emit a source collimated light beam propagating along the source optical path to be at least partially incident upon the reflecting device, reflecting the source collimated light beam via the reflecting device to create a reflected collimated light beam that propagates along the sensor optical path such that the reflected collimated light beam is at least partially incident upon the object to produce a silhouette, wherein at least a portion of the silhouette is incident upon the sensing device to generate initial image data responsive to the silhouette and processing the initial image data to generate resultant image data, wherein the processing includes, generating initial Pitch Diameter data to determine an initial Pitch Diameter (PD) responsive to the silhouette, parameterizing at least a portion of the initial Pitch Diameter and expressing the at least a portion of the initial Pitch Diameter data in a Jacobian Matrix, solving the Jacobian Matrix responsive to a plurality of physical characteristics of the object to generate Correction Factor (CF) data and processing the initial Pitch Diameter (PD) data and the Correction Factor (CF) data to generate resultant Pitch Diameter (PD) data.

A machine-readable computer program code, the program code including instructions for causing a controller to implement a method for measuring physical characteristics of a component using an inspection system, wherein the inspection system includes a light source defining a source optical path, a sensing device defining a sensor optical path, a reflecting device disposed to communicate the source optical path with the sensor optical path and at least one processing device communicated with the sensing device is provided, wherein the method includes associating the object with the inspection system such that the object is disposed within the sensor optical path, operating the light source to emit a source collimated light beam propagating along the source optical path to be at least partially incident upon the reflecting device, reflecting the source collimated light beam via the reflecting device to create a reflected collimated light beam that propagates along the sensor optical path such that the reflected collimated light beam is at least partially incident upon the object to produce a silhouette, wherein at least a portion of the silhouette is incident upon the sensing device to generate initial image data responsive to the silhouette and processing the initial image data responsive to at least one predetermined algorithm to generate resultant image data comprising at least one of a plurality of physical characteristics of the object.

BRIEF DESCRIPTION OF THE DRAWING FIGURES

The foregoing and other features and advantages of the present invention will be more fully understood from the following detailed description of illustrative embodiments, taken in conjunction with the accompanying drawings in which like elements are numbered alike in the several Figures.

DETAILED DESCRIPTION OF THE INVENTION

Figure 1:
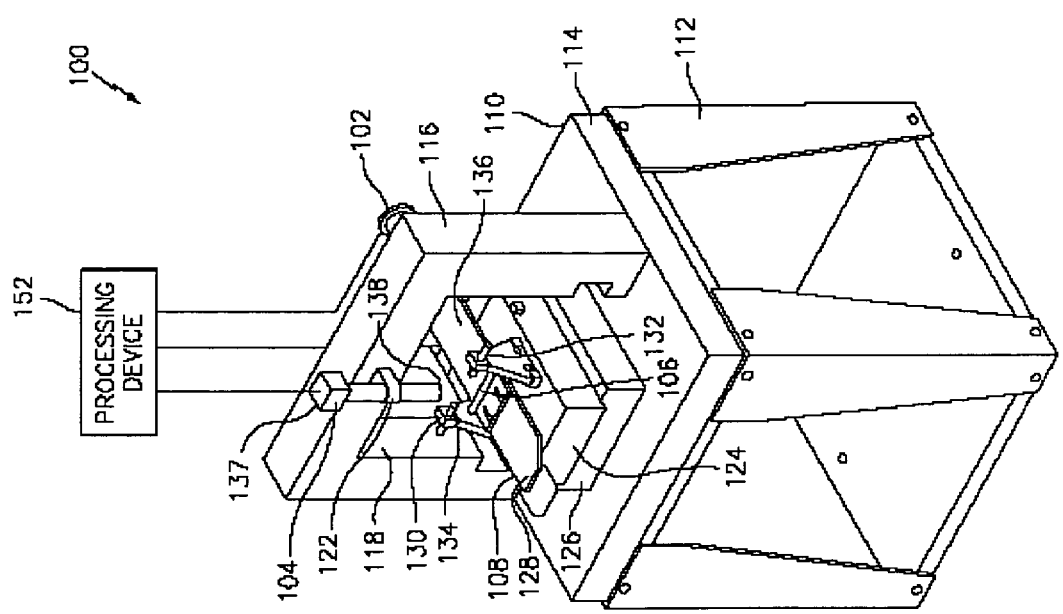
FIG. 1 shows a perspective side view of a component inspection system.
Figure 2:
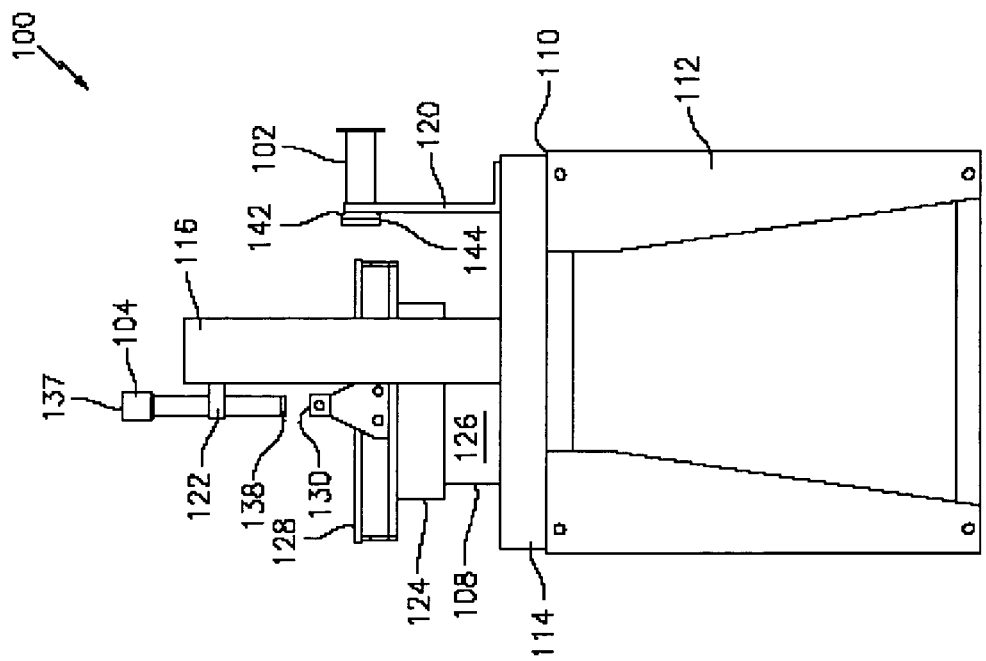
FIG. 2 shows a side view of a component inspection system.
Figure 3:
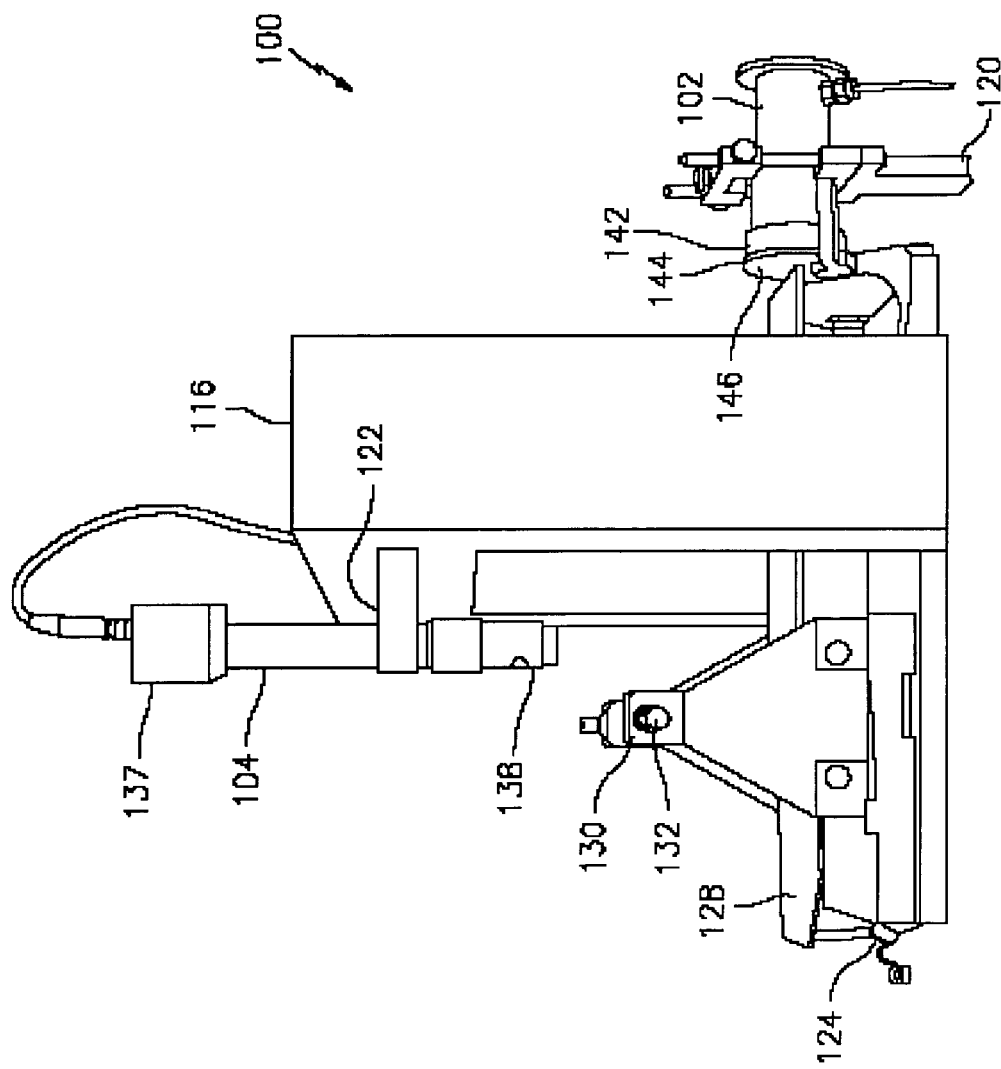
FIG. 3 shows a close up side view of a component inspection system.
Figure 4:
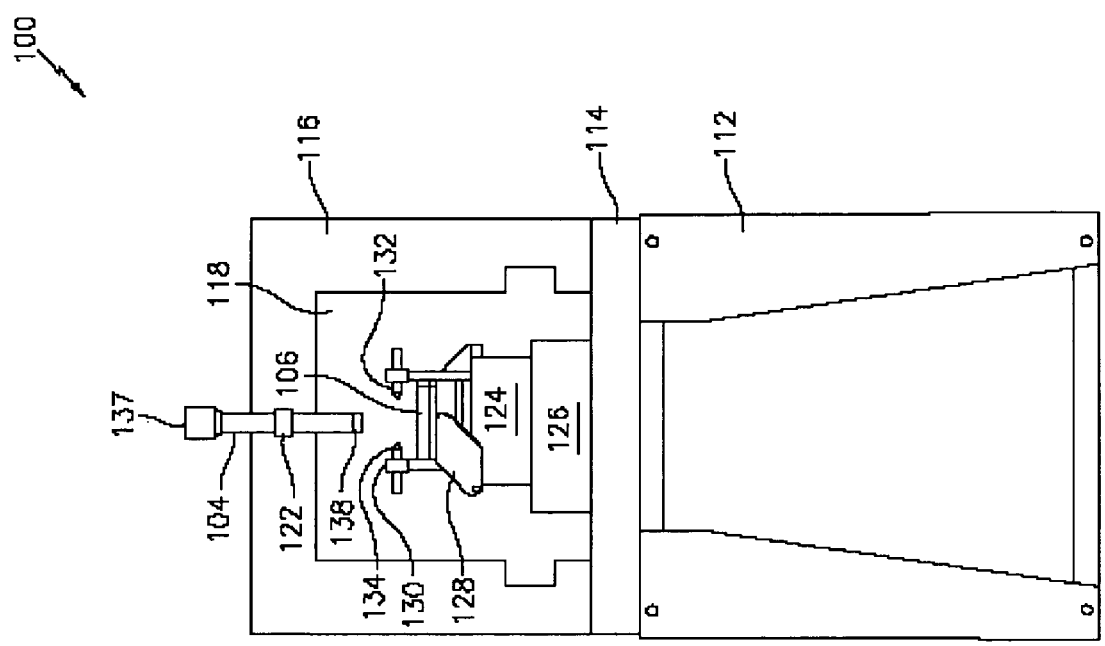
FIG. 4 shows a front view of a component inspection system.
Figure 5:
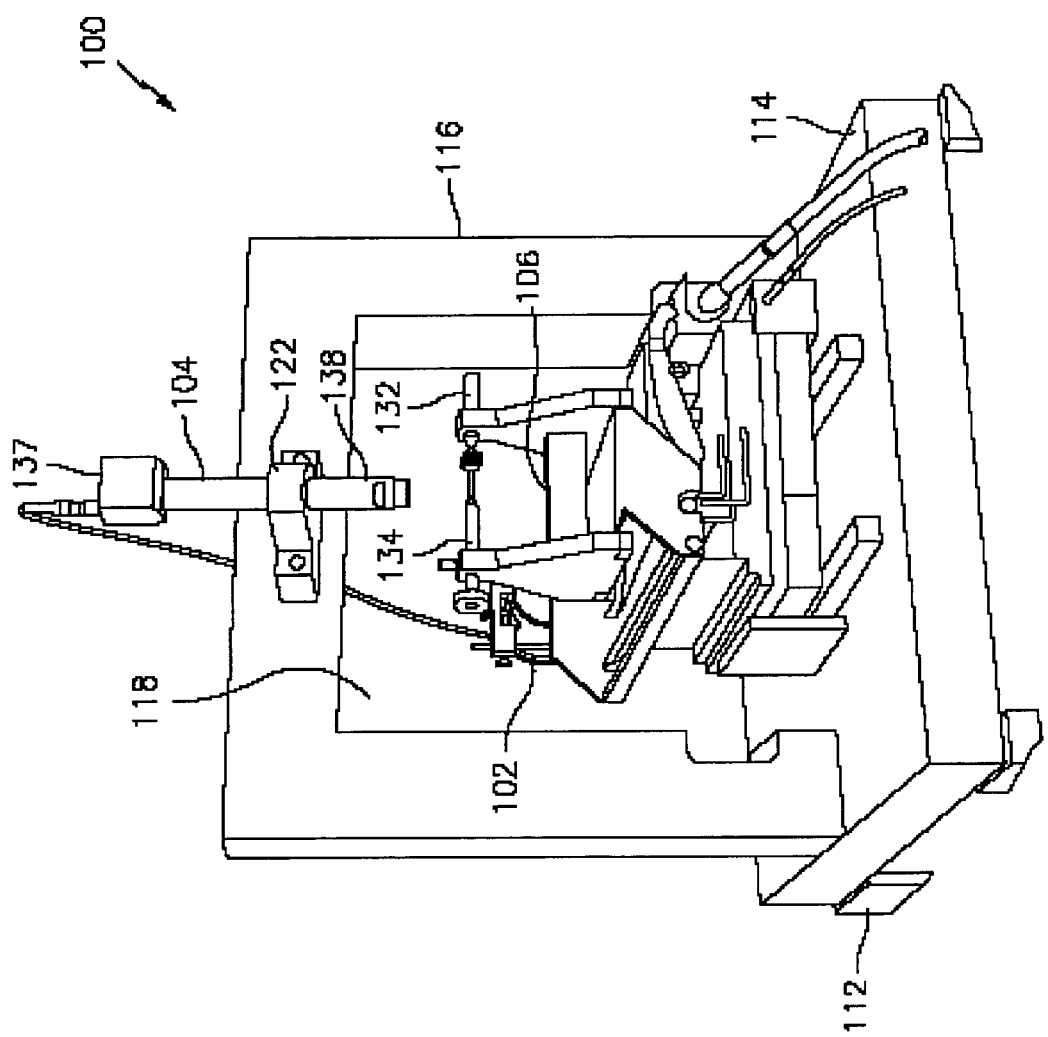
FIG. 5 shows a close up perspective front view of a component inspection system.
Figure 6:
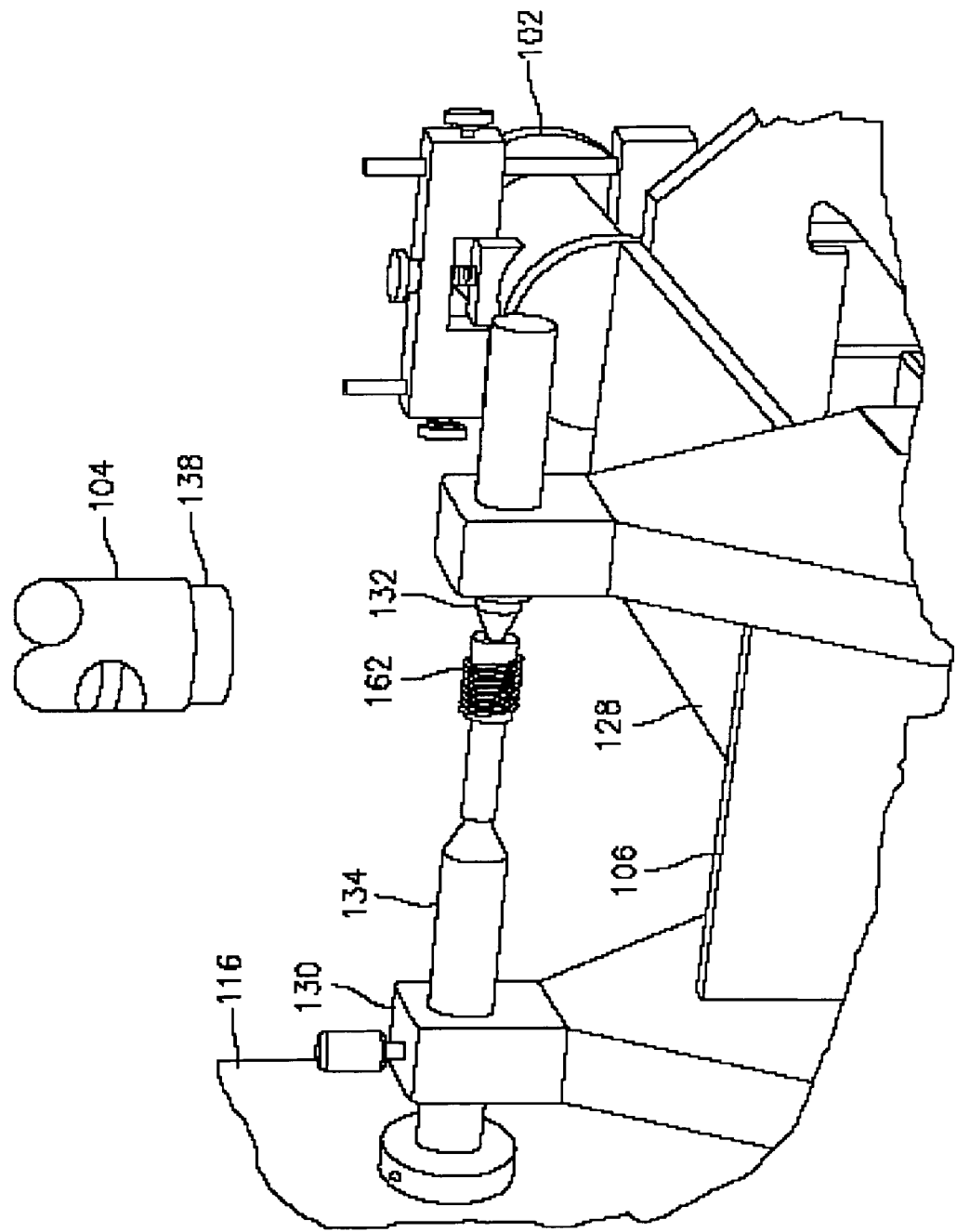
FIG. 6 shows a close up front offset view of a component inspection system having a component disposed between arbors.

An exemplary embodiment is described herein by way of illustration as may be applied to the measurement and inspection of threaded gages and product, such as screws, bolts and other externally threaded components. However, while an exemplary embodiment is shown and described hereinbelow, it should be appreciated by those skilled in the art that the invention is not limited to the embodiment(s) and application(s) as described herein, but also to any component and/or measurement where accuracy in tolerance measurement is critical, such as taps, splines, gears, internal bores, integral plane cylindrical bores, internal threads, internal/external diameters and/or material composition and/or strength. Moreover, those skilled in the art will appreciate that a variety of potential implementations and configurations are possible within the scope of the disclosed embodiments.

Referring to FIGS. 1-8, an inspection system 100 is shown and described. In accordance with an exemplary embodiment, inspection system 100 includes a collimated light source 102, a sensing device 104, a reflecting device 106, a component support device 108 and a system support structure 110. System support structure 110 includes a base support structure 112, a base structure 114, a bridge structure 116 defining a bridge cavity 118, a light source mounting device 120 and a sensor mounting device 122. Base support structure 112 is disposed to be supportingly associated with base structure 114 and base structure 114 is disposed to be supportingly associated with bridge structure 116, wherein bridge cavity 118 is disposed between bridge structure 116 and base structure 114.

Collimated light source 102 may be associated with base structure 114 via light source mounting device 120 such that light emitted from collimated light source 102 propagates along a source optical path which is defined by collimated light source 102 and which is parallel to base structure 114. Sensing device 104 may be associated with bridge structure 116 via sensor mounting device 122, wherein sensing device 104 defines a sensor optical path which perpendicularly intersects the source optical path. Although, base structure 114 and bridge structure 116 may be constructed from a non-metallic polymer casting, it is contemplated that base structure 114 and bridge structure 116 may be constructed from any shock, vibration and/or movement attenuating material(s) and/or composite(s) suitable to the desired end purpose.

Component support device 108 includes a positioning device 124 and a mounting base 126, wherein mounting base 126 is associated with base structure 114. Positioning device 126 includes a positioning stage 128 and a component retainer 130, wherein component retainer 130 is associated with positioning stage 128 and includes a first arbor 132 separated from a second arbor 134 via an arbor cavity 136 and wherein at least one of first arbor 132 and/or second arbor 134 includes a notched potion, or arbor reference "knee" position 220. Positioning stage 128 may be positionally and controllably configurable in all planes (such as x-plane, y-plane, z-plane) relative to mounting base 126 via a motor operated by a motor controller. At least one of first arbor 132 and second arbor 134 are configurable for retaining a component within component retainer 130. Reflecting device 106 may be associated with positioning stage 128 such that reflecting device 106 is disposed at an angle of 45° relative to the surface of positioning stage 128 and such that reflecting device 106 is disposed in the same plane as first arbor 132, second arbor 134 and arbor cavity 136 (i.e. sensor optical path). Additionally, component support device 108 may be disposed within bridge cavity 118 such that reflecting device 106 is disposed at the intersection of the source optical path and the sensor optical path. Although reflecting device 106 is shown as a high quality 0.25 wave length first surface style mirror, reflecting device 106 may be any high quality reflective surface device suitable to the desired end purpose.

Sensing device 104 includes a high resolution camera 137 having a microscope-type telecentric optical lens 138 and although sensing device 104 is shown as being powered via an external power source, sensing device 104 may be powered using any power source suitable to the desired end purpose, such as a battery. Moreover, although microscope type telecentric optical lens 138 is shown as having a magnification factor of 2.6×, microscope type tele-centric optical lens 138 may have any magnification factor suitable to the desired end purpose. Furthermore, although sensing device 104 is a VISICS CCD camera having a microscope type telecentric optical lens system with 2.6× magnification, it is contemplated that sensing device 104 may be any sensing device suitable to the desired end purpose.

Figure 7:
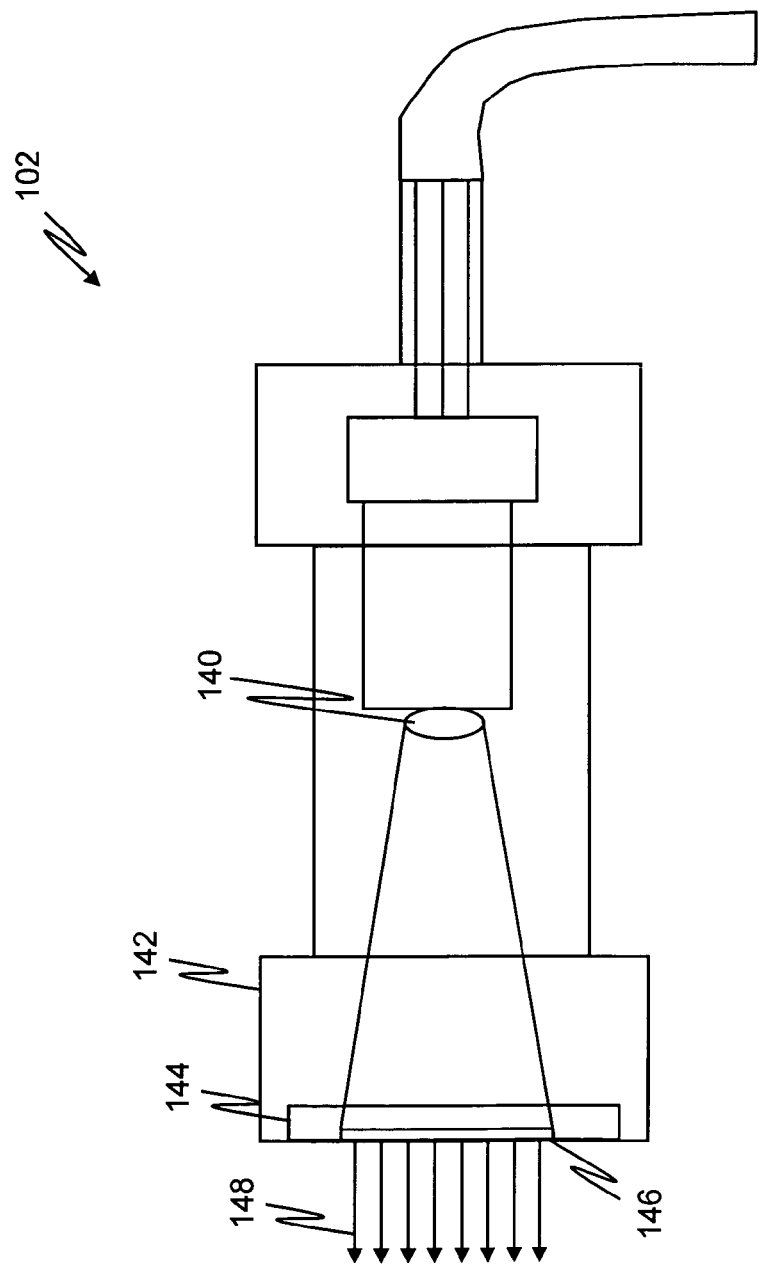
FIG. 7 shows a schematic block diagram of a collimated light source.
Figure 8:
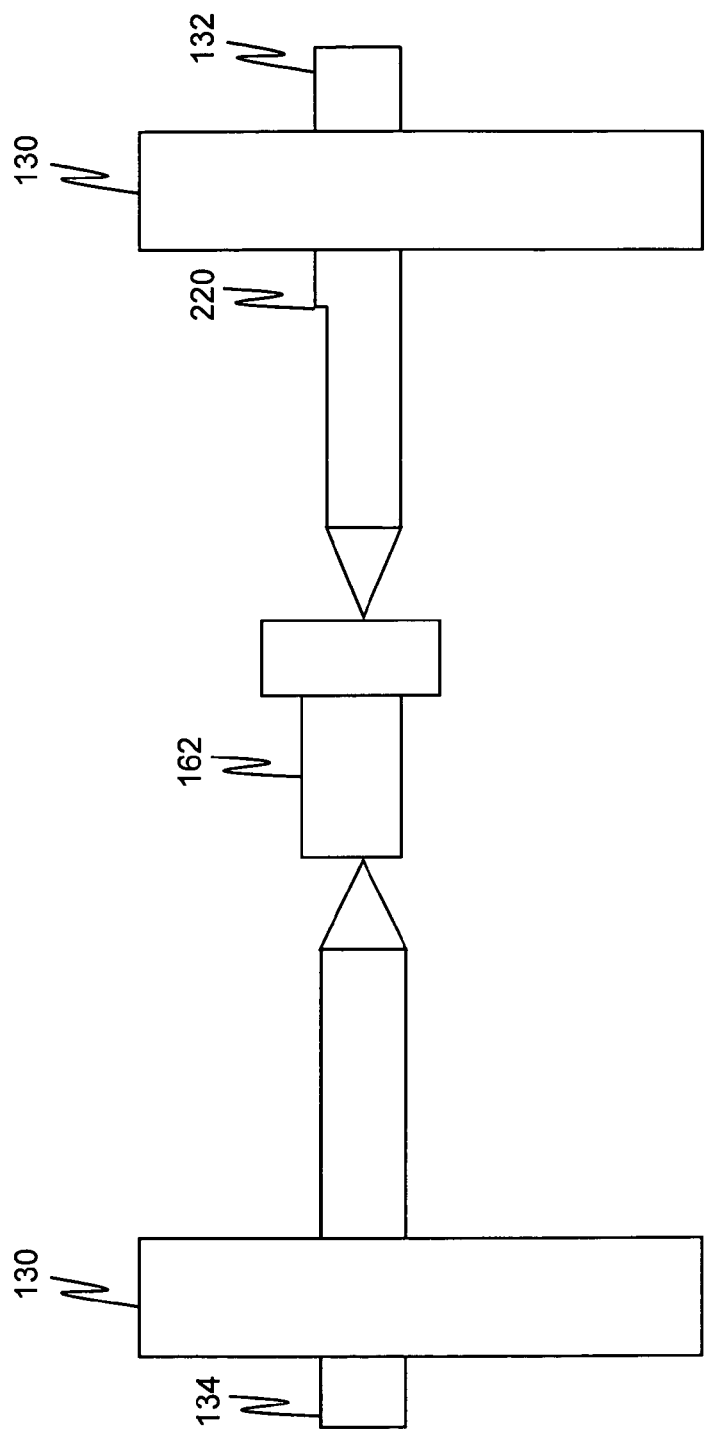
FIG. 8 shows a front view of a component disposed between arbors of a component inspection system.

Referring to FIG. 7, collimated light source 102 includes a Light Emitting Diode (LED) 140, a collimating lens 142 and a lens cap 144 having a lens slot 146 disposed to minimize the stray emission of light emitted from collimating lens 142. In addition, collimated light source 102 may be associated with base structure 114 such that collimating lens 142 is in optical line of sight with reflecting device 106. Moreover, although collimated light source 102 is shown as being powered via an external power source, collimated light source 102 may be powered using any power source suitable to the desired end purpose, such as a battery.

Inspection system 100 is constructed such that when LED 140 is energized a beam of light is emitted from LED 140 and is projected such that the beam of light becomes incident upon collimating lens 142. Collimating lens 142 collimates the beam of light to create a collimated light beam 148, which is then emitted from collimating lens 142. Upon exiting collimating lens 142, collimated light beam 148 propagates along the source optical path and becomes incident upon reflecting device 106, which is disposed at an angle of 45° relative to the surface of positioning stage 128. Reflecting device 106 then reflects incident collimated light beam 148 and the reflected collimated light beam 150 propagates along the sensor optical path to become incident upon sensing device 104. However, because reflecting device 106 is disposed in the same plane as first arbor 132, second arbor 134 and arbor cavity 136 (i.e. sensor optical path), before reflected collimated light beam 150 becomes incident upon sensing device 104, reflected collimated light beam 150 becomes incident upon first arbor 132, second arbor 134 and arbor cavity 136. As such, when a component is disposed within component retainer 130 to be between first arbor 132 and second arbor 134, reflected collimated light beam 150 becomes partially blocked by the component, first arbor 132 and/or second arbor 134 and as a result, a shadow or silhouette of the component, first arbor 132 and/or second arbor 134 is created and communicated to sensing device 104.

Figure 9:
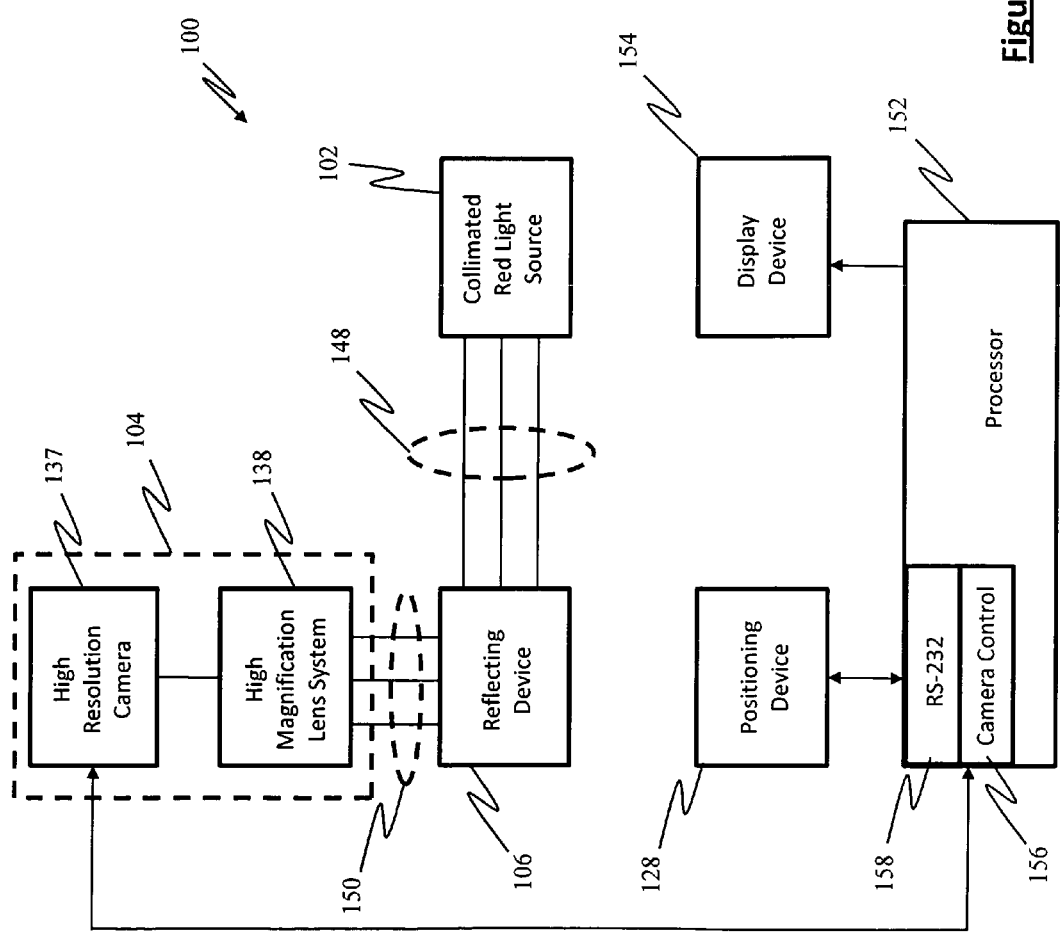
FIG. 9 shows a schematic block diagram of a component inspection system.

Referring to FIG. 9, an overall block diagram of inspection system 100 is shown and described. Inspection system 100 is shown as including a processing device 152 having a display device 154, camera controller circuitry 156 and a communications port 158, wherein processing device 152 is disposed to be in communication with collimated light source 102, sensing device 104 and positioning device 124. In accordance with an exemplary embodiment, collimated light source 102 is shown in optical communication with reflecting device 106 such that collimated light beam 148 emitted from collimated light source 102 is incident upon reflecting device 106. Reflecting device 106 reflects collimated light beam 148 to produce reflected collimated light beam 150. Sensing device 104 is shown in optical communication with reflecting device 106 such that reflected collimated light beam 150 is incident upon sensing device 104 to be received by high resolution camera 137 via microscope type tele-centric optical lens 138. Thus, when a component is disposed between first arbor 132 and second arbor 134, the silhouette of the component, first arbor 132 and/or second arbor 134 is also received by high resolution camera 137.

High resolution camera 137 converts the silhouette image into image data and communicates this image data to processing device 152, wherein the image data is responsive to the interaction between the component and reflected collimated light beam 148 received by telecentric optical lens 138. Processing device 152 then examines this image data to determine if more image data is required. If more image data is required, processing device 152 instructs sensing device 104 to obtain more image data. If necessary, processing device 152 may control the position of positioning device 126 via communications port 158 to dispose positioning device 126 as necessary in a manner responsive to the desired image data. Although processing device 152 is shown as being communicated with positioning device 126 via an RS-232 or RS-422 communications port, processing device 152 may be communicated with positioning device 126 via any device and/or method suitable to the desired end purpose, such as via wireless communications. Moreover, camera controller circuitry 156 may be communicated with processing device 152 via any method and/or device suitable to the desired end purpose. Furthermore, although high resolution camera 137 is shown as an electronic camera being able to support an image size of up to at least 1296×1016 pixels, high resolution camera 137 may be any high resolution camera 137 suitable to the desired end purpose.

It is further contemplated that, although display device 150 is shown as a flat panel display device having a 1280×1024 display capability, display device 150 may be any display device and/or method suitable to the desired end purpose. Additionally, although processing device 152 is shown as a computer system operating an MS Windows 2000 operating system (or higher version) and having a Pentium processor with at least 128 Mb RAM, Ethernet network capability and a wireless communications device, such as a modem, DSL or T1 line, processing device 148 may be any processing device suitable to the desired end purpose. Positioning device 126 may also include a cast iron stage with a glass slide and a linear motor having crossed rollers with patented anti-creep technology. The linear motor allows for at least plus and minus three (3) inches of travel in both X and Y axes and allows for a maximum load of at least 635 Kg. Positioning device 126 may also include a digital motor (servo) controller having an integral drive with a digital current loop and is communicated with processing device 152 via an RS-232/RS-422 communications port. Additionally, the digital motor (servo) controller may be capable of supporting a 10-30 amp peak, 6-15 amps continuous and a 170-300 VDC bus and although the digital motor (servo) controller shown as being capable of supporting movement in the X and Y axis, it should be appreciated that digital motor (servo) controller may also be capable of supporting movement in the Z axis, as well.

Figure 10:
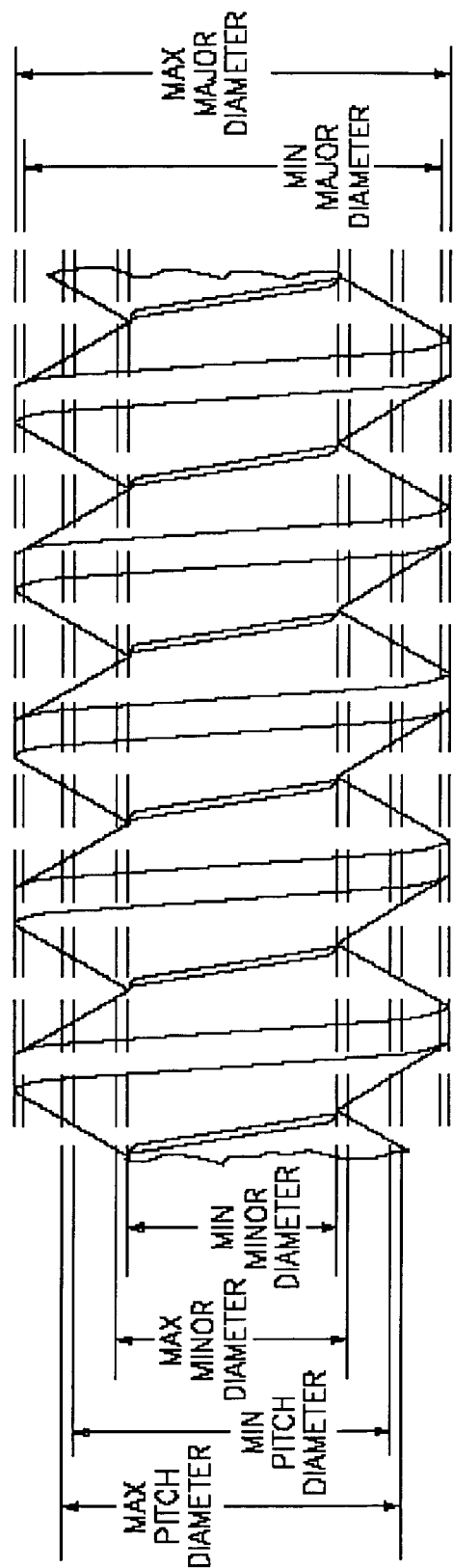
FIG. 10 shows a side view of a threaded component.
Figure 11:
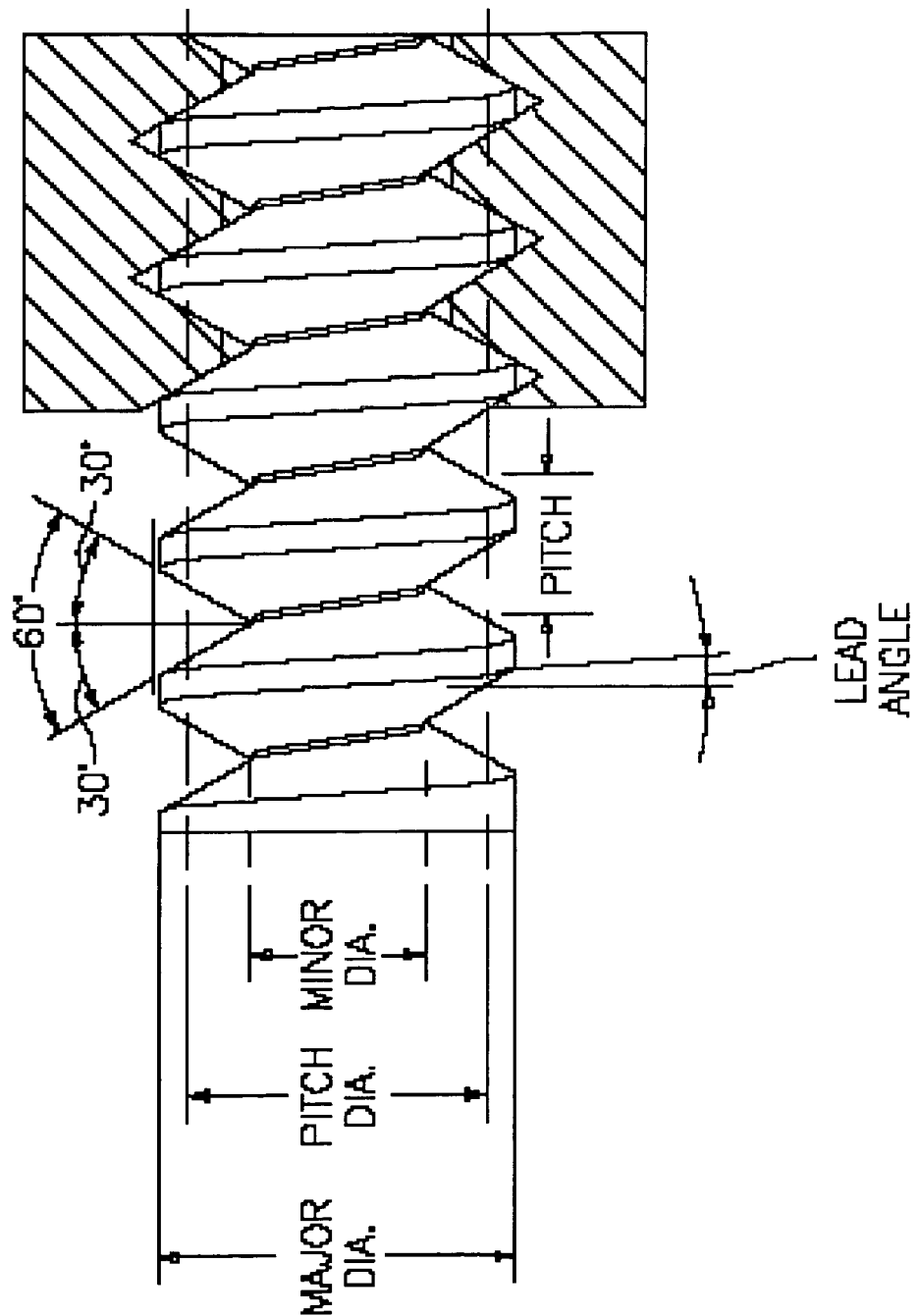
FIG. 11 show a side view of a threaded component.

Referring to FIG. 10 and FIG. 11, a side view of an externally threaded component, such as a threaded product is shown and discussed. A component thread is a combination of a thread ridge and groove, typically of uniform section, that is produced by forming a groove with a helix on an external or internal surface of a cylinder or cone. Because the component thread is designed to operate in association with an opposing component thread, it is essential that certain key physical characteristics relating to thread size and thread form be tightly controlled. As such, it is desirable to measure these thread size characteristics and thread form characteristics as accurately as possible. The thread size characteristics include the major diameter, the minor diameter, the functional diameter and the pitch diameter and the thread form characteristics include the pitch, the lead, the uniformity of helix angle, the flank angle and the included angle, each one of which is discussed in more detail hereinbelow.

The major diameter of the component is the diameter or width of an imaginary cylinder, called the major cylinder, whose surface would be parallel to the straight axis of the component and whose surface would bound the crests of an external thread or the roots of an internal thread. However, although both threaded gages and threaded products typically have a full form major diameter, threaded gages also typically have a truncated major diameter. As such, a threaded gage includes a full form major diameter and a truncated major diameter and a threaded product only includes a full form major diameter. The full form major diameter, for both a threaded gage and a threaded product, may be defined as a composite measurement responsive to the major radius (which may be defined as the distance between the component axis and one surface of the major cylinder or one half of the major diameter) measured on the 0° side of the full form threads and the major radius measured on the 180° side of the full form threads. However, for a threaded gage, the truncated major diameter may be defined as a composite measurement responsive to the major radius measured on the 0° side of the truncated threads and the major radius measured on the 180° side of the truncated threads.

The minor diameter of the component is the diameter of an imaginary cylinder, or minor cylinder, whose surface would be parallel to the straight axis of the component and whose surface would bound the roots of an external thread or the crests of an internal thread. Thus, the minor radius, which may be defined as the distance between the component axis and one surface of the minor cylinder or one half of the minor diameter, and which is typically measured using the first thread on the 0° side, is typically determined using a best fit radius that is tangential to the flanks and that has no reversals.

The pitch of a thread having uniform spacing may be defined as the distance, measured parallel to the axis, between corresponding points on adjacent thread forms in the same axial plane and on the side of the axis. Thus, the pitch may be defined as the number of threads per inch (TPI) and the pitch distance may be defined as 1/TPI, wherein TPI is measured parallel to the thread axis, from a point on one flank to the corresponding point on the next available flank. The pitch diameter of the component is the diameter or width of an imaginary cylinder, called the pitch cylinder, whose surface would be parallel to the axis of the thread or component and whose surface would intersect the profile of a straight thread such that the width of the thread ridge and the thread groove are equal.

Thus, the pitch diameter of a threaded gage, which typically includes full form threads and truncated threads, includes a pitch diameter front and a pitch diameter back, wherein the pitch diameter front is responsive to the leading and trailing angles of the thread, the lead and the crest width of the threads at the truncated location and wherein the pitch diameter back is responsive to the leading and trailing angles of the thread, the lead and the crest width of the threads at the full form location. Whereas the pitch diameter of a threaded component, which typically includes only full form threads, includes only a pitch diameter front, wherein the pitch diameter front is responsive to the leading and trailing angles of the thread, the lead and the crest width of the threads.

The lead may be defined as the axial distance moved by the component in relation to the amount of angular rotation, when a threaded component is rotated about its axis with respect to a fixed mating thread. Thus, the lead is the amount of axial travel when the threaded component is turned one full turn or 360° and pitch is the distance measured parallel to the axis from a point on one flank to the corresponding point on the adjacent flank. Any deviation in lead tends to increase the functional diameter of the external thread (or decrease the functional diameter of the internal thread) and rapidly consumes the allowed operating pitch diameter tolerance of a threaded component. A deviation in lead may result in non-engagement of a screw thread with its mating part at all but a few points. Thus, when the threaded parts are assembled, and torque is applied, the result is pressure being applied to only a few, and possibly only one pressure flank. As such, any deviation in lead may produce a non-engagement condition for some threads and cause a failure in engaging threads at the point of pressure flank engagement due to non-engagement.

The helical path deviation of a thread is a wavy deviation from a true helical advancement or a non-uniformity of helix angle. In a similar manner as the lead, a deviation in the helical path causes an increase in the functional size of the component in proportion to the amount of waviness. Thus, all of the statements that were made concerning a deviation in lead also apply to a deviation in helical path and similarly, a deviation of helical path may result in partial engagement of the thread flanks with the result that torque pressures may not be evenly distributed and may result in pre-load relaxation.

The included angle of a thread is the angle between the flanks of the thread measured in an axial plane. The flank angles are the angles between the individual flanks and the perpendicular to the axis of the thread measured in an axial plane. A flank angle of a symmetrical thread is commonly referred to as the half included angle or the half angle of a thread. A deviation in the flank angle may result in a failure of the thread when the product is exposed to line loads or when torque is applied. This is because an improper flank engagement may create an unevenly distributed pressure load along the flank rather than the pressure load being distributed evenly along the flank.

Other important physical characteristics of the component include the functional size diameter, the taper characteristic of the pitch cylinder and the out-of-roundness, all of which can generate a non-engagement condition. In fact, distortion or deviation from specifications of any of the physical characteristics discussed herein may cause varying degrees of non-engagement.

The functional, or virtual, diameter of a thread (external or internal) may be defined as the resultant size of the product thread taking into account the effect of lead, helical path deviation, flank angle deviation, taper and out-of-roundness. As such, it may be seen that the functional diameter is the pitch diameter of the enveloping thread of perfect pitch, lead and flank angles, having full depth of engagement, but that are clear at crests and roots, of specified lengths of engagement. For an external thread, the functional diameter may be derived by adding the cumulative effects of deviations to the pitch diameter (for internal threads subtracting the cumulative effects of deviations), including variations in lead and flank angles over a specified length of engagement. Thus, it should be clear that the effects of taper, out-of-roundness and surface defects may be positive or negative on either external or internal threads, respectively.

The taper characteristic of the pitch cylinder is simply a tapering of the pitch cylinder of the thread. As can be seen, a tapered thread fails to give a complete thread engagement, which may lead to a product failure caused by uneven torque pressure conditions on pressure flanks and pre-load relaxation.

The out-of-roundness of the pitch cylinder, which is any deviation of the pitch cylinder from round, limits the thread engagement and allows for only line contact with the mating thread and typically includes two types of out-of-roundness: Multi-lobe or Oval.

With the desired physical characteristics of a threaded component to be measured explained hereinabove, an overall method for measuring these characteristics is provided and described hereinbelow. Furthermore, it is contemplated that each of the methods, calculations and algorithms described herein, may be performed via a system operator and/or via an automated system.

Figure 12:
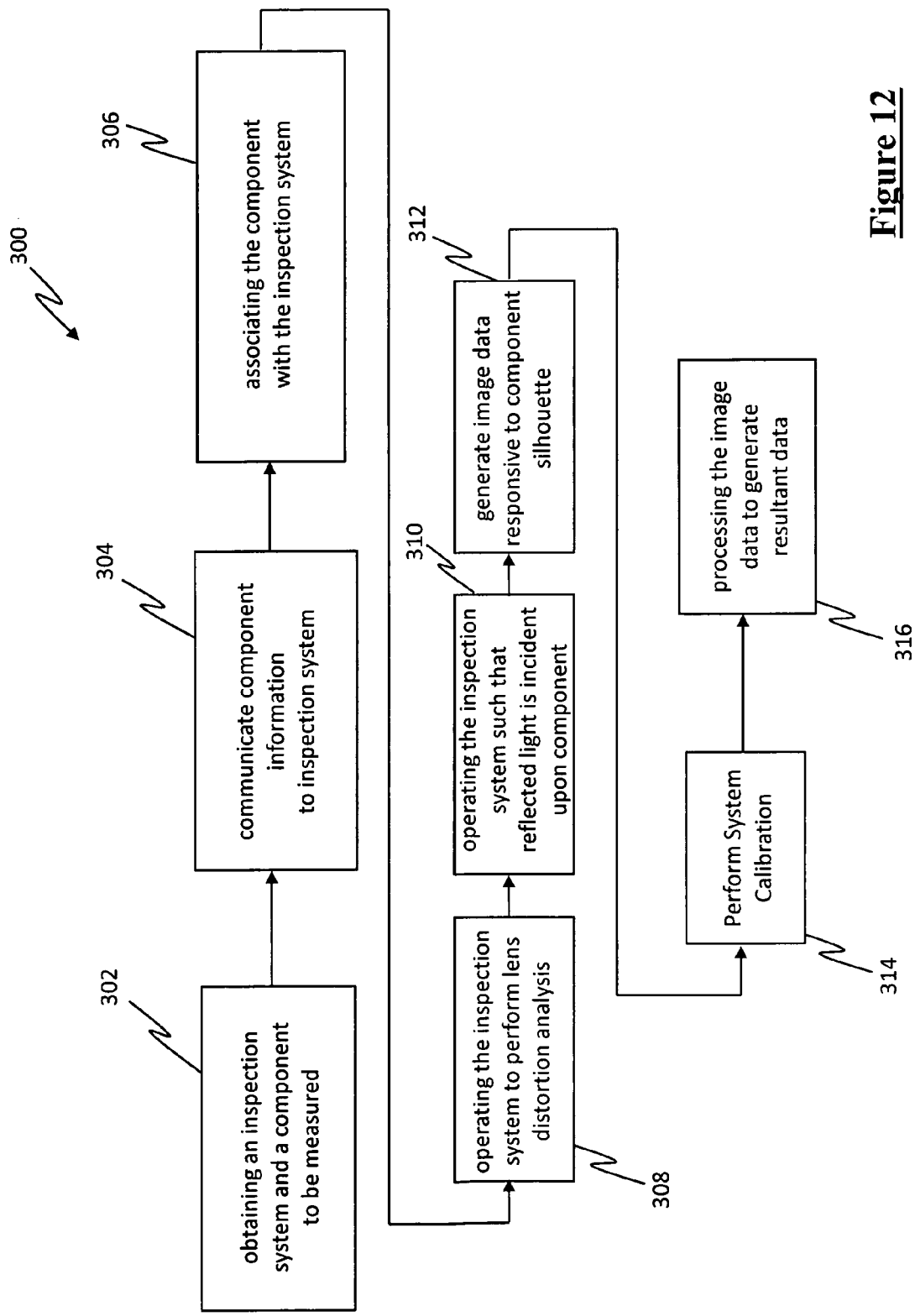
FIG. 12 shows a block diagram illustrating an overall method for measuring the characteristics of a component using a component inspection system.

Referring to FIG. 12, an overall method 300 for measuring the characteristics of a component using inspection system 100 is shown and discussed. In accordance with an exemplary embodiment, inspection system 100 and component 162 may be obtained, as shown in block 302, wherein inspection system 100 includes a light source 102, a sensing device 104, a reflecting device 106, and a component support device 108. Information regarding the type of threaded component 162 such as a screw, gage, bolt and/or other component, to be measured is determined and communicated to inspection system 100 via system software, as shown in block 304. Although, this may be accomplished via a system operator who enters information regarding threaded component 162 into processing device 152 via a mouse or keyboard in a manner responsive to a component/gage selection algorithm 400. It should be appreciated that component information may be stored in a database and retrieved via sensors, such as bar code readers.

Once component 162 has been selected and component information communicated to processing device 152 has been completed, component 162 is associated with inspection system 100 to be disposed within component support device 108, as shown in block 306. This may be accomplished by a system operator disposing component 162 within component retainer 130 such that component 162 is retained within arbor cavity 136 via first arbor 132 and second arbor 134. Inspection system 100 is then operated to perform a pre-calibration lens distortion analysis to determine any parabolic lens distortion factors, as shown in block 308. This pre-calibration lens distortion analysis is a curve fitting routine that is performed prior to the calibration procedure and that is separate from the system lens distortion measurement and correction that is part of the calibration procedure and that is used to compensate for any parabolic distortion that is inherent in optical lens 138. Moreover, although the lens distortion analysis is provided by the lens manufacturer, it should be appreciated that any suitable lens distortion analysis method may be independently developed and/or used.

In order to perform this analysis, collimated light source 102 emits a collimated light beam that becomes incident upon reflecting device 106, thus causing a reflected collimated light beam to become incident upon sensing device 104. Sensing device 104 receives this reflected collimated light beam and generates image data responsive to this reflected collimated light beam. Because the reflected collimated light beam is unimpeded, the image data generated by sensing device 104 is only responsive to the characteristics of collimated light source 102, reflecting device 106 and sensing device 104. Thus, the image data may be examined to determine if lens 138 of sensing device 104 contains any imperfections or distortions. As such, processing device 152 examines the image data to determine whether any variations of image intensity exist within a predefined field of view of lens 138. This may be accomplished by examining portions of the generated image data responsive to a number of various image locations within the field of view of lens 138, wherein the examined portions are responsive to locations within the vertical and horizontal span of the field of view, ranging from the bottom to the top and from the left hand side to the right hand side of the field of view.

For example, the image data to be examined may include data points responsive to a plurality of locations on lens 138 that represent the vertical span of lens 138 (or of the field of view of lens 138) for both the 0° and 180° side of at least one arbor. The results for each of these data points, which represent the actual vertical distortion characteristics of lens 138, may then be plotted on an actual vertical gradient chart (and compared with an ideal vertical gradient chart provided by the manufacturer of lens 138, wherein the ideal vertical gradient chart represents the ideal lens characteristics. In a similar fashion, the image data to be examined may also include data points responsive to a plurality of locations on lens 138 that represent the horizontal span of lens 138 (or of the field of view of lens 138). As above, the results for each of these data points, which represent the actual horizontal distortion characteristics of lens 138, are then plotted on an actual horizontal gradient chart and compared with an ideal horizontal gradient chart provided by the manufacturer of lens 138, wherein the ideal horizontal gradient chart represents ideal lens characteristics. Any deviations between the actual vertical/horizontal gradient charts and the ideal vertical/horizontal gradient charts are recorded and stored for later application in subsequent calculations and/or measurements. It should be noted that, in order to minimize any effect of lens distortion on the measurements, the areas of interest, i.e. areas of component 162 to be measured, are almost always disposed in the center of the field of view for lens 138.

Once this has been completed, inspection system 100 is operated to cause positioning stage 128 to be disposed such that the reflected collimated light beam is incident upon component 162, as shown in block 310. The reflected collimated light beam incident upon component 162 produces a silhouette of component 162 and/or first arbor 132 which is projected to be incident upon sensing device 104. Sensing device 104 generates image data responsive to silhouette of component 162 and first arbor 132 and communicates this image data to processing device 152 which processes the image data to generate resultant data, as shown in block 312. Processing device 152 then instructs inspection system 100 to perform a system calibration in a manner responsive to a predetermined calibration algorithm 500, as shown in block 314. Upon completion of predetermined calibration algorithm 500, inspection system 100 performs a component measurement in a manner responsive to a predetermined component measurement algorithm 600, predetermined calibration algorithm 500 and/or the results of lens distortion analysis, as shown in block 316. Once the component measurement has been completed, component information is then displayed to the system operator via display device 154 and/or via a printed certificate or report. In accordance with an exemplary embodiment, component/gage selection algorithm 400, predetermined calibration algorithm 500 and predetermined component measurement algorithm 600 are discussed in more detail below.

Figure 13:
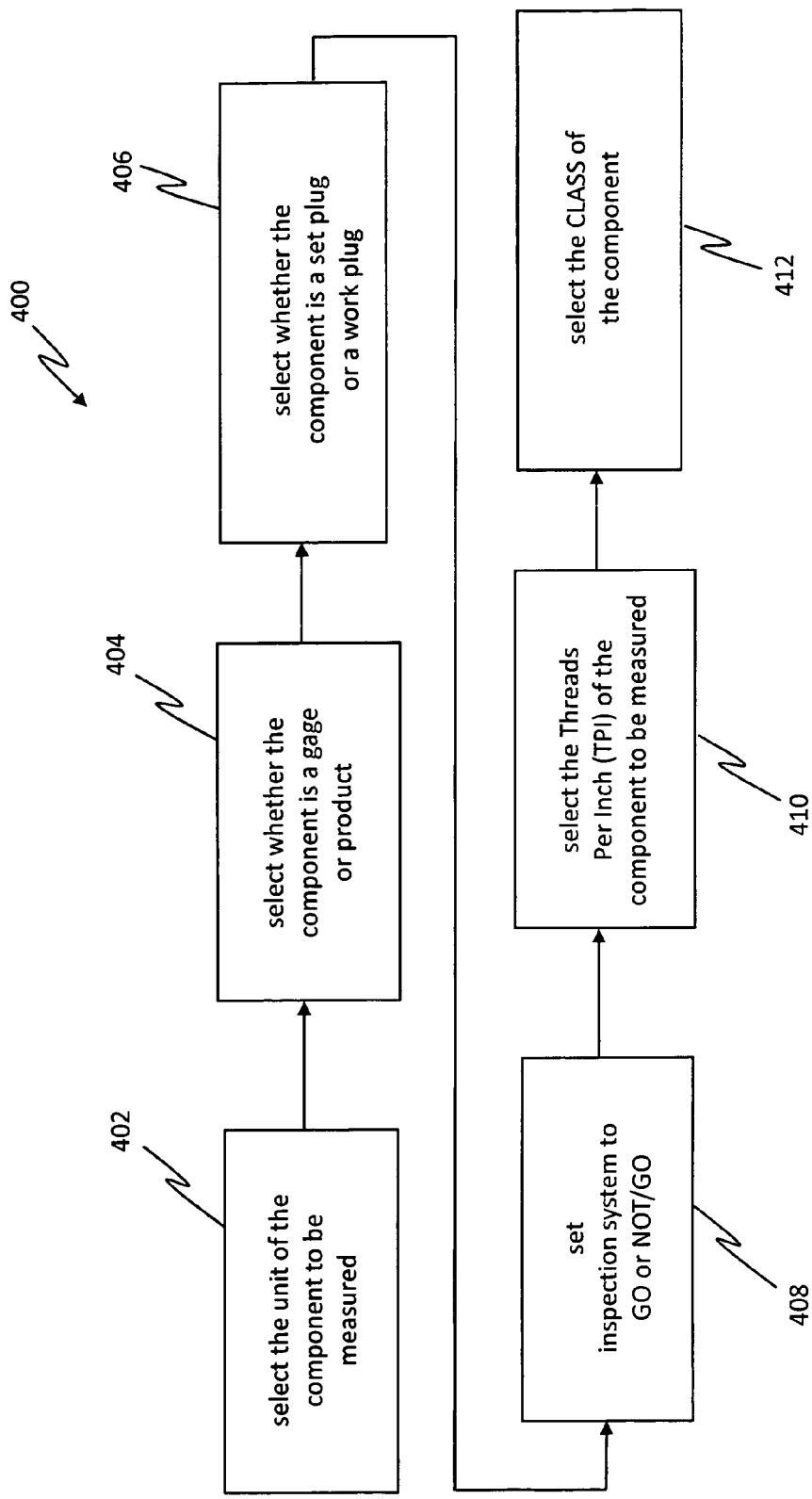
FIG. 13 shows a block diagram illustrating a component/gage selection algorithm.

Referring to FIG. 13, a block diagram of a component/gage selection algorithm 400 is shown and described. It should be noted that although component/gage selection algorithm 400 is described for component/gage selection screen 214 herein, as configured for a threaded product, component/gage selection algorithm 400 may be modified as required for various component selections.

Figure 14:
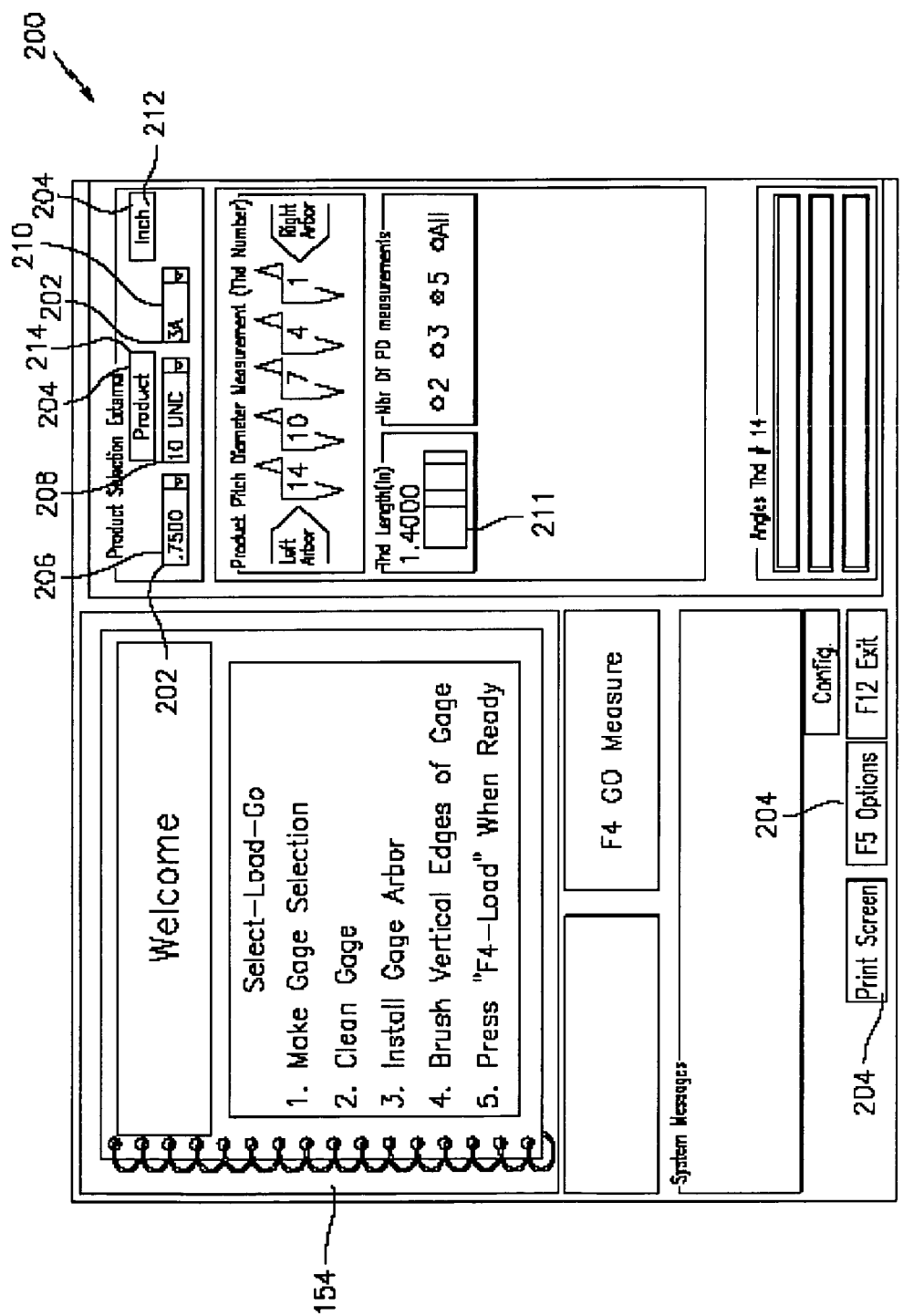
FIG. 14 shows a GUI screen capture of a component/gage selection screen.

Referring to FIG. 14, upon starting inspection system 100, a component/gage selection screen 200 is displayed to a system operator via display device 154. Component/gage selection screen 200 may be created in a Graphical User Interface (GUI) format having a plurality of pull-down menus 202 and software buttons 204 that allow known physical characteristics of a component to be measured to be communicated to inspection system 100 via a mouse and/or keyboard. Pull-down menus 202 may include at least one of a component size selection pull down menu 206, a TPI pull down menu 208, a Class selection pull down menu 210 and a thread length pull down menu 211 and software buttons 204 may include at least one of a unit selection button 212, a component selection button 214, a set plug/work plug selection button 216 and a go/not go selection button 218. It should be appreciated that component selection button 214 allows for the selection of a plurality of types of components to be inspected, including a plain diameter gage, a threaded gage, a product, an X-calibration block, a Y-calibration block and a Roll. It should also be appreciated that pull-down menus 202 and software buttons 204 may be displayed to a system operator in a manner responsive to component selection button 214.

Figure 15:
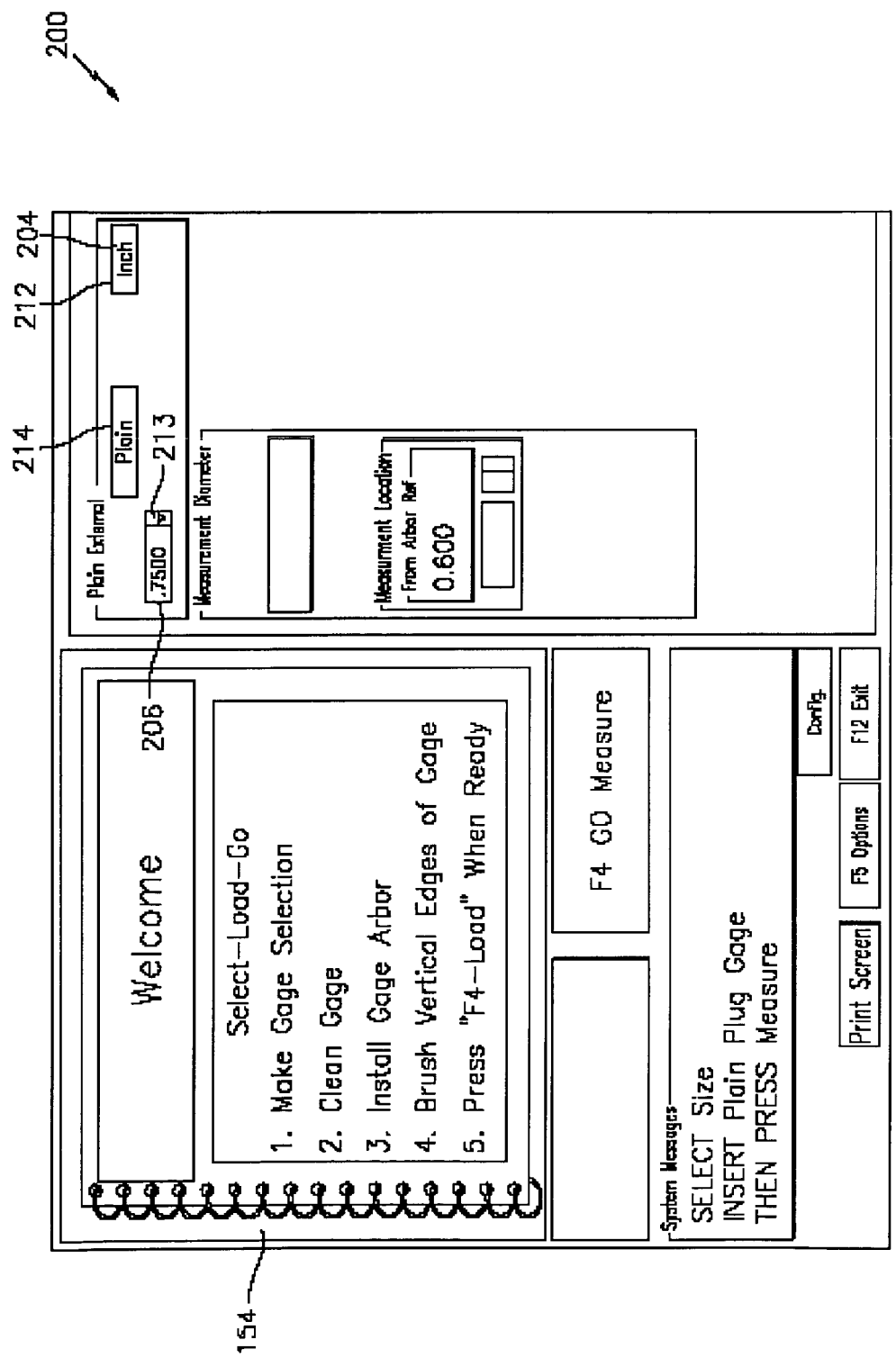
FIG. 15 shows a GUI screen capture of a component/gage selection screen.
Figure 16:
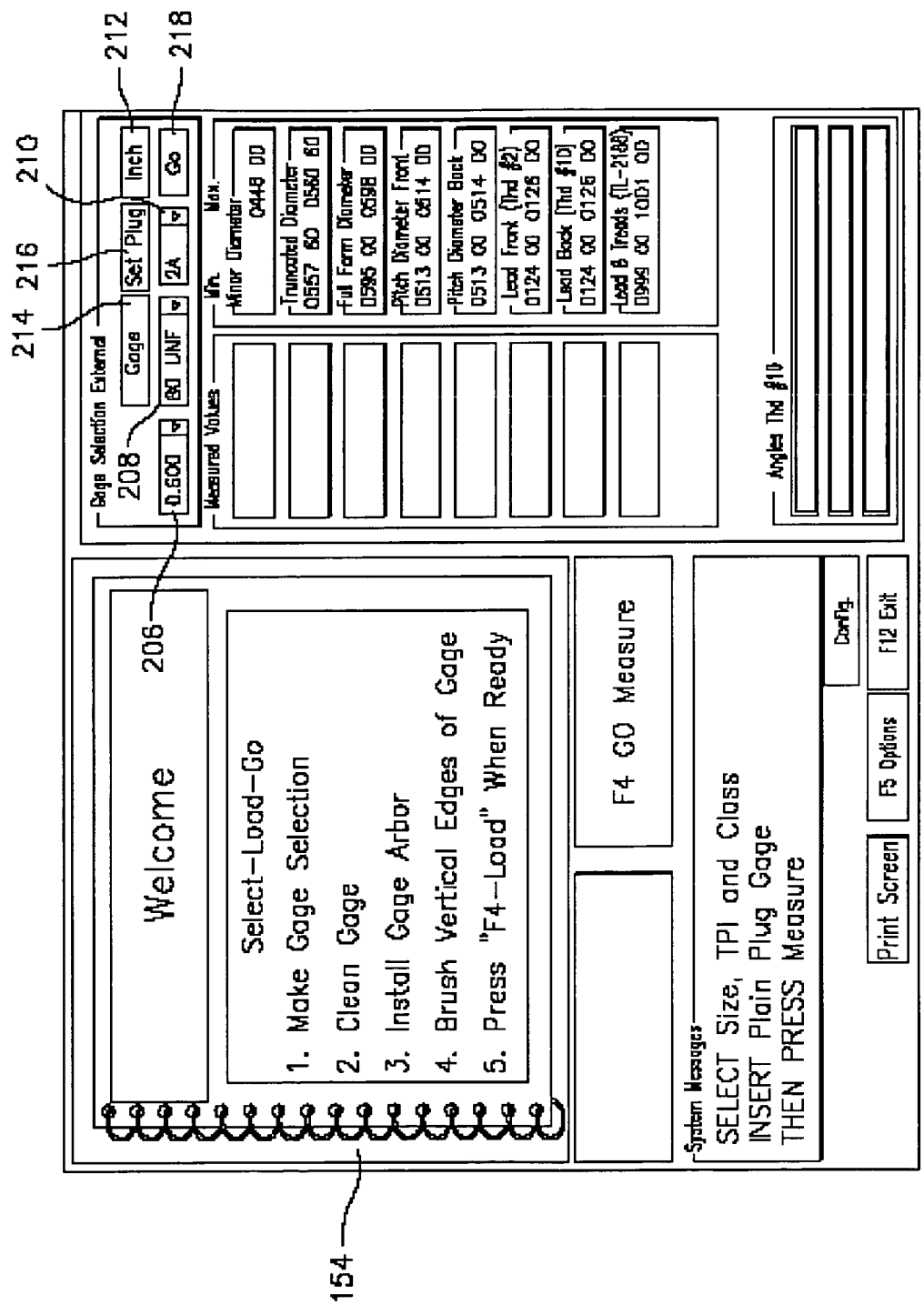
FIG. 16 shows a GUI screen capture of a component/gage selection screen.
Figure 17:
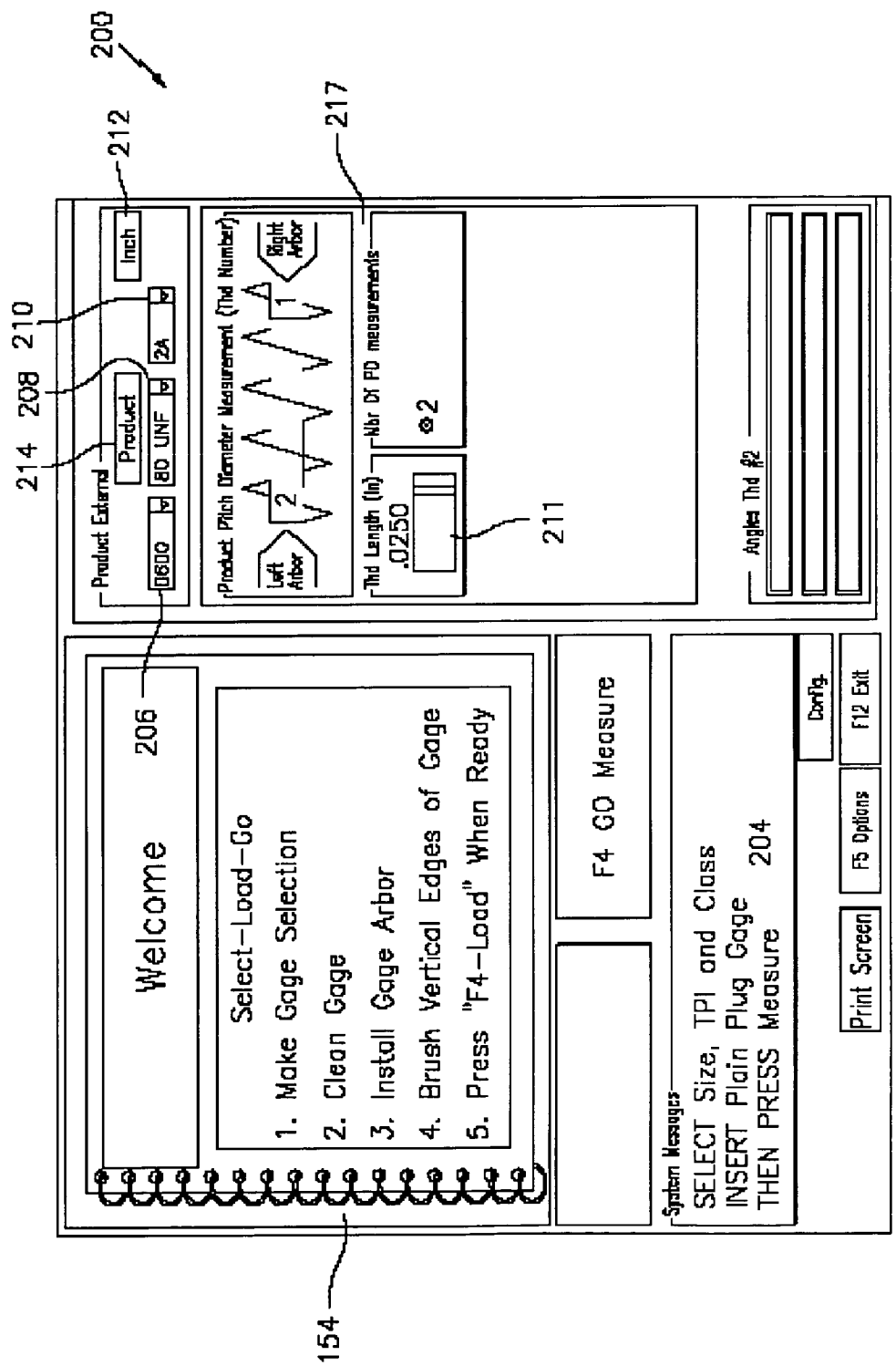
FIG. 17 shows a GUI screen capture of a component/gage selection screen.
Figure 18:
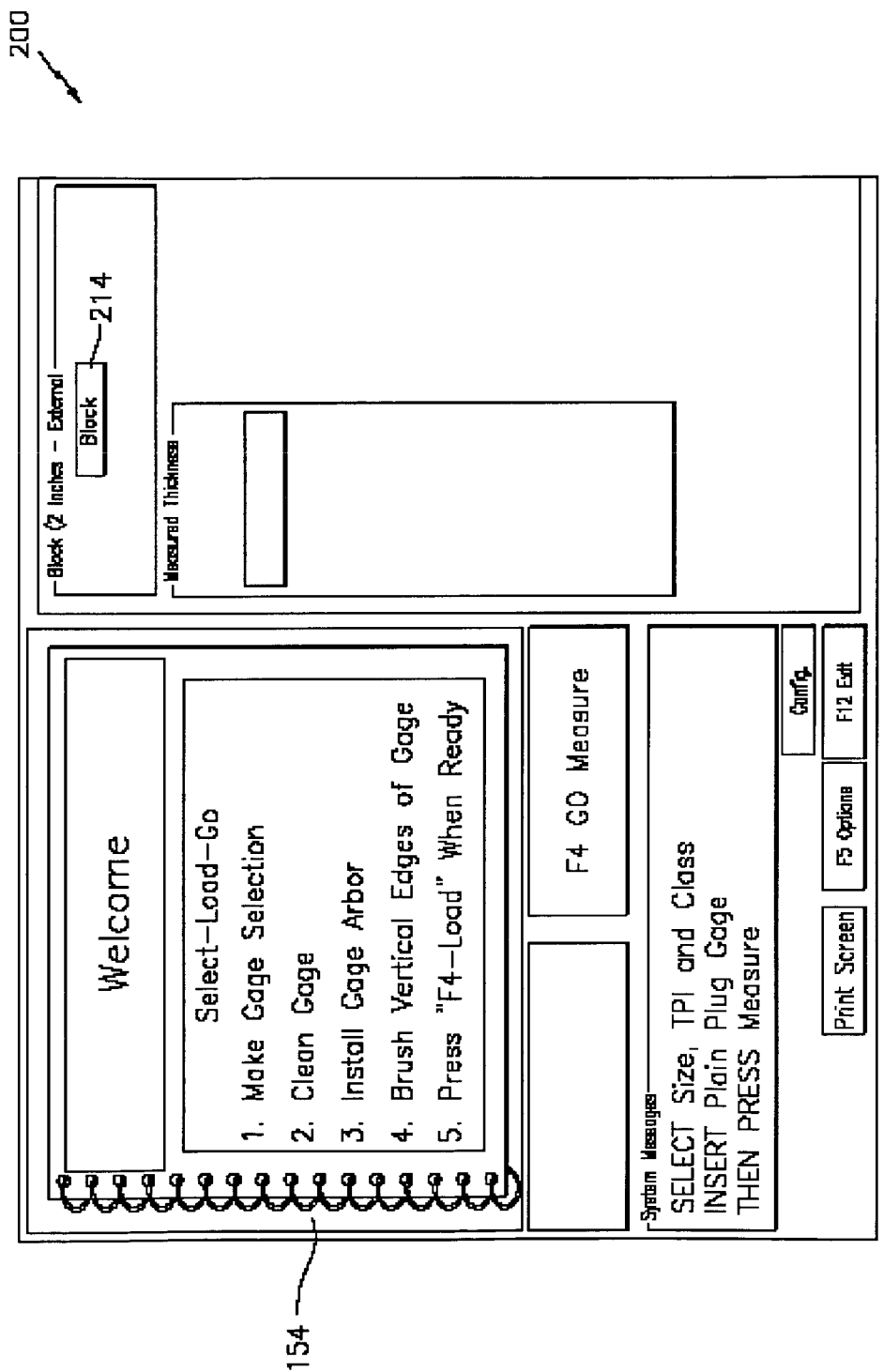
FIG. 18 shows a GUI screen capture of a component/gage selection screen.

For example, referring to FIG. 15, if component selection button 214 is configured for a plain diameter gage, plurality of pull-down menus 202 and plurality of selection buttons 204 displayed to a system operator include at least one of a unit selection button 212 and a plain diameter gage size pull down-menu 213. Referring to FIG. 16, if component selection button 214 is configured for a threaded gage, plurality of pull-down menus 202 and plurality of selection buttons 204 displayed to a system operator include at least one of unit selection button 212, set plug/work plug selection button 216, go/not go selection button 218, component size selection pull down menu 206, TPI pull down menu 208 and Class selection pull down menu 210. Referring to FIG. 17, if component selection button 214 is configured for a threaded product, plurality of pull-down menus 202 and plurality of selection buttons 204 displayed to a system operator include at least one of a unit selection button 212, set plug/work plug selection button 216, go/not go selection button 218, component size selection pull down menu 206, TPI pull down menu 208, Class selection pull down menu 210 and a thread length menu 211. Additionally, when component selection button 214 is configured for a threaded product, a pitch diameter measurement menu 217 may be displayed. Referring to FIG. 18, a component/gage selection screen 202 is shown for component selection button 214 configured for a calibration block.

In the case of a threaded component 162, once component/gage selection screen 200 is displayed, the system operator selects the system of units inspection system 100 is to use when measuring threaded component 162, such as English or Metric units, via unit selection button 212, as shown in block 402. The system operator then selects the type of component that inspection system 100 will be measuring (i.e. a threaded component), via gage/product selection button 214, as shown in block 404, and (in the case of a gage) whether it is a set plug or a work plug, via set plug/work plug selection button 216, as shown in block 406. Also in the case of a gage, once this has been accomplished, the system operator selects whether this is a go or not/go, via go/not go selection button 218, and the gage size of the component is selected, via gage size selection pull-down menu 206, as shown in block 408. In the case of a component, the Threads Per Inch (TPI) and the Class of the component are then selected, via TPI pull down menu 208, as shown in block 410 and Class selection pull down menu 210, respectively, as shown in block 412.

Figure 19:
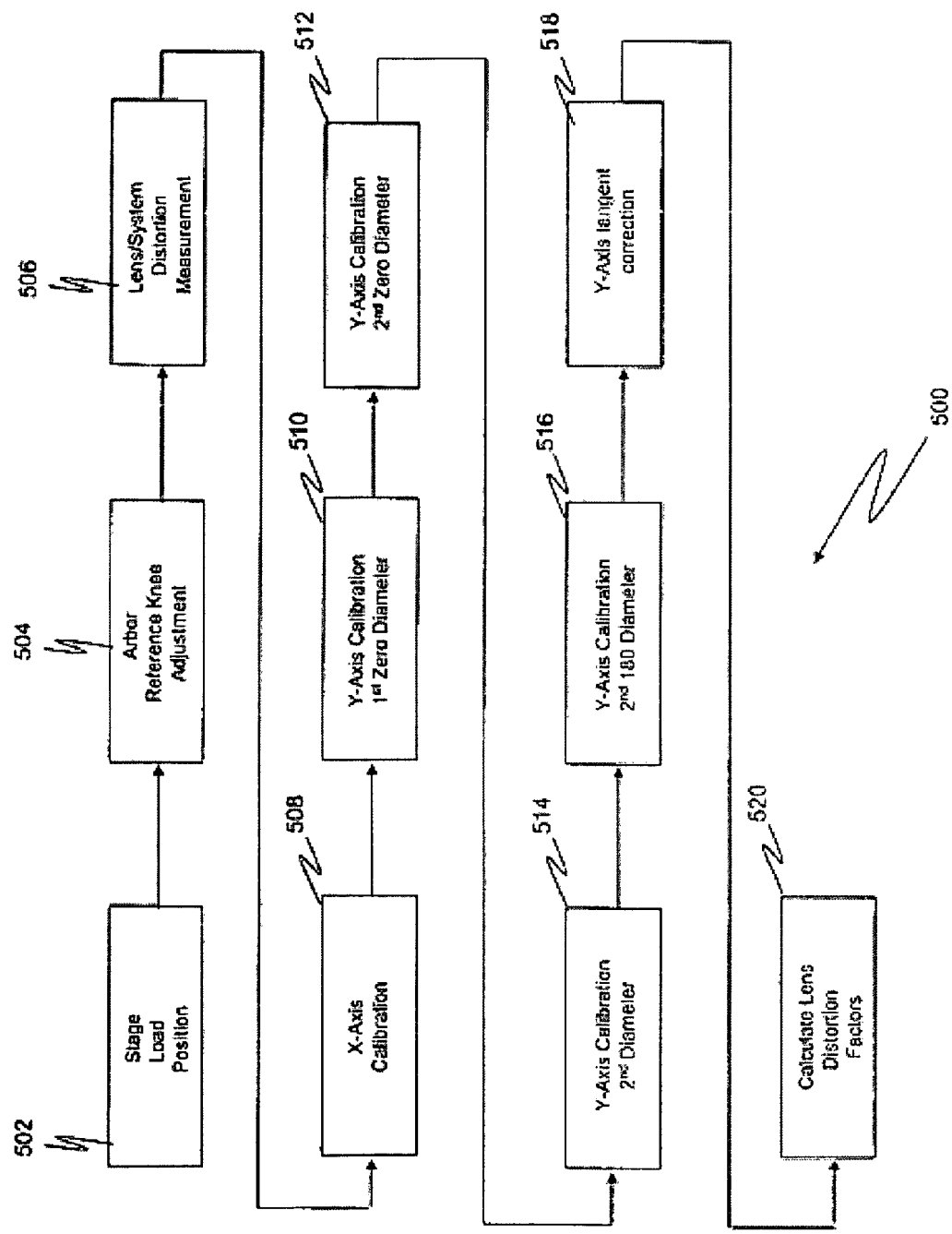
FIG. 19 shows a block diagram illustrating a calibration algorithm.
Figure 20:
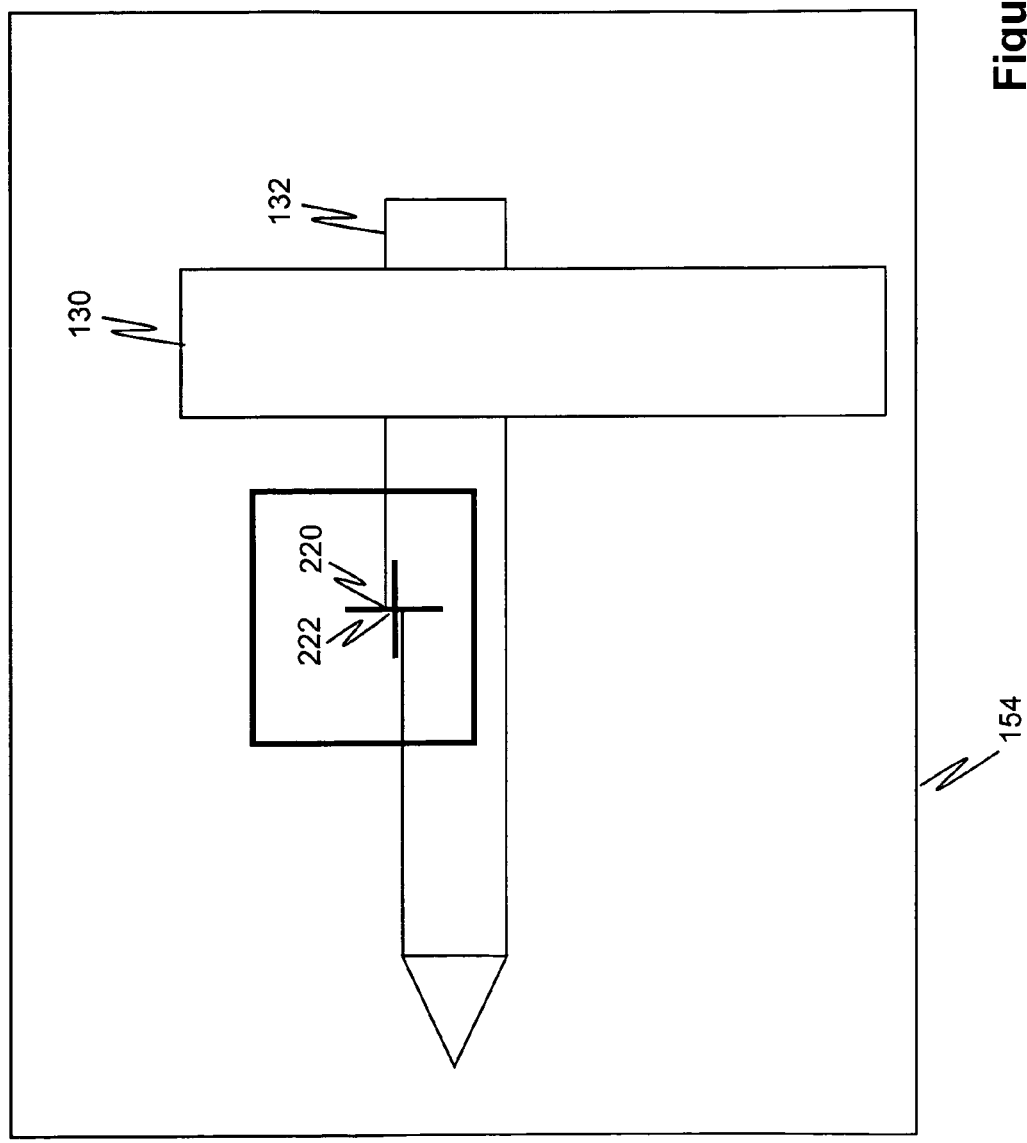
FIG. 20 shows a reference arbor knee and a search box.

Upon completion of the system startup procedure, inspection system 100 begins performing a system calibration procedure responsive to predetermined calibration algorithm 500. Referring to FIG. 19 and FIG. 20, once the system calibration procedure has been initiated, positioning stage 128 is moved to a predetermined starting position, or HOME position, as shown in block 502. It is contemplated that any location of positioning stage 128 may be selected as the HOME position. At this point, all encoders are zeroed and all positional measurements are determined with reference to this HOME position. An Arbor reference adjustment is then performed to properly locate the arbor reference "knee" position 220, as shown in block 404, wherein arbor reference "knee" position 220 is a notch disposed on at least one of first arbor 132 and/or second arbor 134. A software "constraint window" or search box is created within the field of view of lens 138 and image data representing the image contained within this search box is then examined to locate arbor reference "knee" position 220. Arbor reference "knee" position 220 may be located by analyzing this image data for differences in pixel intensities to identify where the horizontal arbor surface ends and the vertical arbor surface begins. This vertical arbor surface is arbor reference "knee" position 220. Once arbor reference "knee" position 220 is located, blue crosshairs 222 are disposed at arbor reference "knee" position 220 and displayed to the system operator via display device 154 to allow the system operator to visually confirm arbor reference "knee" position 220. It should be stated that arbor reference "knee" position 220 must be contained with this search box for predetermined calibration algorithm to continue. If arbor reference "knee" position 220 is not disposed within the search box, predetermined calibration algorithm terminates.

Figure 21:
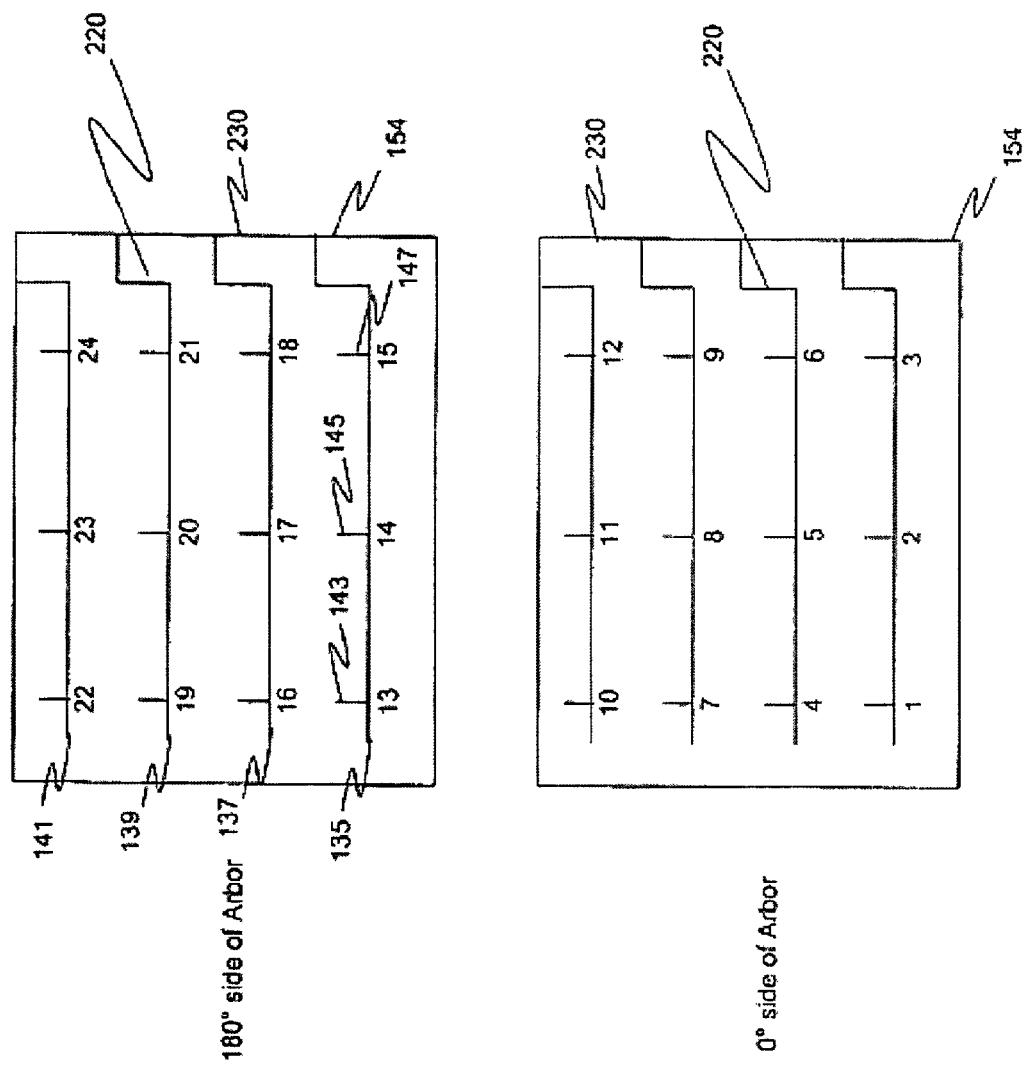
FIG. 21 shows a display device illustrating lens distortion measurements.

In accordance with an exemplary embodiment, the lens system distortion measurements are then conducted, as shown in block 506. Referring to FIG. 21, this may be accomplished by operating inspection system 100 such that positioning stage 128 relocates arbor reference "knee" position 220 to four distinct position/locations within the field of view of lens 138 on the 0° side of at least one of first arbor 132 and/or second arbor 134. These four distinct position/locations are located at a lower vertical field of view position 135, a lower middle vertical field of view position 137, a upper middle vertical field of view position 139 and an upper vertical field of view position 141. At each of these four vertical locations, three horizontal measurements are made and include a left measurement 143, a center measurement 145 and a right measurement 147. This measurement data may be obtained by observing and/or analyzing the image data corresponding to the particular points of measurement. The results of this observation/analysis may then be recorded for use in subsequent calculation. This sequence is then repeated on the 180° side of at least one of first arbor 132 and/or second arbor 134. It should be appreciated that a total of 24 measurements (i.e. 12 on the 0° side and 12 on the 180° side) are stored and thus, become part of the calculated lens distortion measurement performed near the end of the calibration cycle. As discussed above, the lens system distortion routine, and thus the distortion equations, may be provided by the manufacturer of lens system 138 or may be generated responsive to the component to be inspected.

Once the lens system distortion measurements have been conducted, the X-Axis calibration is performed, as shown in block 508. The X-Axis calibration may be accomplished by locating the center position, the left extreme and the right extreme of field of view 230 of lens 138 and using these data points to calculate the inches per step, inches per pixel and/or the steps per inch calibration factors for the X-Axis. One way to determine center position, left extreme and right extreme of field of view 230 is to move arbor reference knee position 220 to the extreme left hand side of field of view 230 and register this location as the left extreme. Arbor reference knee position 220 is then moved to the extreme right hand side of field of view 230 and this location is registered as the right extreme. Arbor reference knee position 220 should then be moved to a point midway between the left extreme and the right extreme of field of view 230. This point will be the center of field of view 230 and should be registered as the center position. This ensures minimal distortion from lens 138.

Upon completion of the X-Axis calibration, a Y-Axis calibration at the $1^{st}$ 0° diameter is performed, as shown in block 510. The Y-Axis calibration at the $1^{st}$ 0° diameter may be accomplished by using the lower middle center location and upper middle center location obtained during the lens system distortion measurement to calculate the inches per step, inches per pixel and/or the steps per inch calibration factors for the Y-Axis. The lower middle vertical location is then determined and is used to measure the radius for the 0° side (which may later be added to the radius for the 180° side to determined the diameter of the arbor).

Upon completion of the Y-Axis calibration at the $1^{st}$ 0° diameter, a Y-Axis $2^{nd}$ 0° diameter determination is performed, as shown in block 512. The determination of the Y-Axis $2^{nd}$ 0° diameter may be accomplished by moving positioning stage 128 such that arbor reference knee position 220 on the 0° side of the arbor is disposed at a lower vertical location, a lower middle vertical location, an upper middle vertical location and an upper vertical location of field of view 230. At each of these locations, inspection system 100 performs three horizontal measurements, a left horizontal measurement, a center horizontal measurement and a right horizontal measurement. This data may be stored and may become part of the calculated lens distortion factors determined toward the end of the calibration cycle. It should be appreciated that the lower middle vertical location may be the final position to be measured and may be used to measure the radius for the 180° side, which may later be added to the radius of the 0° side to determine the arbor diameter.

Upon completion of the Y-Axis $2^{nd}$ 0° diameter determination, a Y-Axis $2^{nd}$ diameter determination is performed, as shown in block 514. The determination of the Y-Axis $2^{nd}$ diameter may be accomplished by moving the left arbor reference location to determine the location of the arbor relative to the right arbor reference and lens 138. A single measurement is taken in the center of field of view 230 to minimize distortion and is used to determine the radius and to compute the tangent correction factor that is used to compensate for any misalignment of the Y-Axis of positioning stage 128 with the Y-Axis of lens 138.

Once this has been completed, a Y-Axis $2^{nd}$ 180° diameter determination is performed, as shown in block 516, by moving positioning stage 128 to the 180° side (same X-Axis position) to measure the radius. The Y-Axis tangent correction factor is then determined, as shown in block 518. This compensates for a component that may be disposed between first arbor 132 and second arbor 134 in a non-level (i.e. horizontal) manner. Moreover, this may be accomplished by using the measurements taken at the right and left sides of the arbor and both the X and Y measurement information from the encoders and the image measurement tools are used to compute the tangent correction factor. It should be noted that all subsequent Y-Axis measurements include this compensation factor. All of the information obtained above are then used to determine the lens distortion factor, as shown in block 520, which is then used for all subsequent X and Y measurements, including any light source and/or system stage positional distortions/errors (i.e. Abbe* stage errors).

It is contemplated that predetermined component measurement algorithm 600 is responsive to the component being measured. As such, predetermined component measurement algorithm 600 is explained for various types of components to be measured and includes a threaded product and a threaded gage. It should be appreciated that all measurements may be conducted by observing and/or analyzing image data to determine desired points of interest on threaded component 162, such as the thread ridges and grooves. These points of interest may be located by examining the image data and identifying variations in pixel intensities to establish silhouette edge points of threaded component 162. Once these points of interest have been identified, desired physical characteristics of threaded component 162 may be determined using known mathematical, geometric and/or trigonometric relationships.

Figure 22:
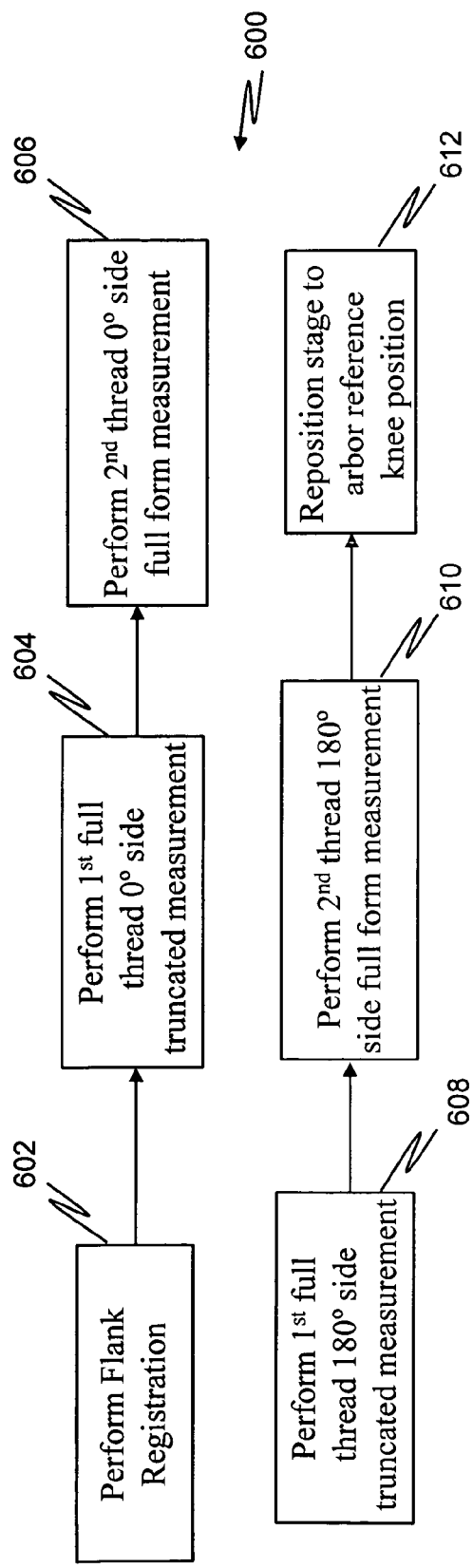
FIG. 22 shows a block diagram illustrating a component measurement algorithm.

Upon completion of predetermined calibration algorithm 500, positioning stage 128 is positioned back to arbor reference knee position 220 and component measurement algorithm 600 is initiated, as shown FIG. 22. At this point, the Flank registration is performed, as shown in block 602. This may be accomplished by disposing positioning stage 128 such that component 162 is positioned to an initial X and Y location by moving positioning stage 128 one half inch away from arbor reference knee position 220 in the X direction and toward component 162. Positioning stage 128 is then moved in the Y direction such that the lower limit of the pitch diameter at the centerline of field of view 230 is approximated. A software measurement tool is then placed at the centerline to find the flank angel crossings at the centerline. The stage is then moved again away from arbor reference knee position 220 in the X-axis direction to align the minor diameter with the left edge of field of view 230. All subsequent measurements rely on moving in pitch lead increments in the X-axis direction. It should be noted that the pitch lead increments are determined by the component selection and are published at the top of the Lead Standards readouts. It should be appreciated that, for threaded gages, the truncated measurements will be conducted at thread #2 and the full form measurements will be conducted at thread #6. The term 4× refers to the number of threads for the third lead measurement and indicates that it is being made over a span of four threads and the term /10 indicates that there are ten threads available on this component.

Once the flank registration has been performed, the $1^{st}$ full thread 0° side truncated measurements are conducted, as shown in block 604. This may be accomplished by repositioning positioning stage 128 on the first thread on the 0° side designated as the truncated thread location. This designation is dependent upon the thread numbers and thus upon the selection of component 162. Using the silhouette image data, processing device 152 then determines the minor radius, the major radius (for set plug only), the pitch radius, the lead pitch, the lead/trail flank angles and the included angles. The major radius is determined via the major diameter, which is a composite measurement based on the major radius of the 0° and corresponding 180° side of the threads. Thus, the major radius is determined by summing the individual measurements along the thread flat and dividing by the number of measurements collected. The number of measurement locations may be determined by taking 70% of the thread width, as determined by predetermined thread tables, and centering them on the center of the thread. This major radius average is then combined from both the 0° and the 180° sides to get the major diameter. For a gage, this process is performed for both truncated and full form locations and for a product, this process is performed only for the full form location.

The pitch diameter calculation (for both truncated and full form location), which is based on the leading and trailing angles, major diameter, pitch lead and crest width at the location in question (i.e. truncated or full form), may be determined by the equation:

$$PD=MD-(Cot(PL/2)-CW),$$

Where, PD is pitch diameter, MD is major diameter, PL is pitch lead and CW is crest width. The lead front measurement, which is responsive to the difference between the groove distance and the ridge distance along the leading/trailing/leading flanks may be determined by positioning a software measurement tool along the X-axis and moving the tool vertically around the pitch diameter until the groove distance minus the ridge distance is minimized. The tool is then repositioned at the minimized location and the groove distance and the ridge distance are added to determine the lead front. The lead back measurement, which is responsive to the difference between the groove distance and the ridge distance along the trailing/leading/trailing flanks may similarly be determined by positioning a software measurement tool along the X-axis and moving the tool vertically around the pitch diameter until the groove distance minus the ridge distance is minimized. The tool is then repositioned at the minimized location and the groove distance and the ridge distance are added to determine the lead back.

Figure 24:
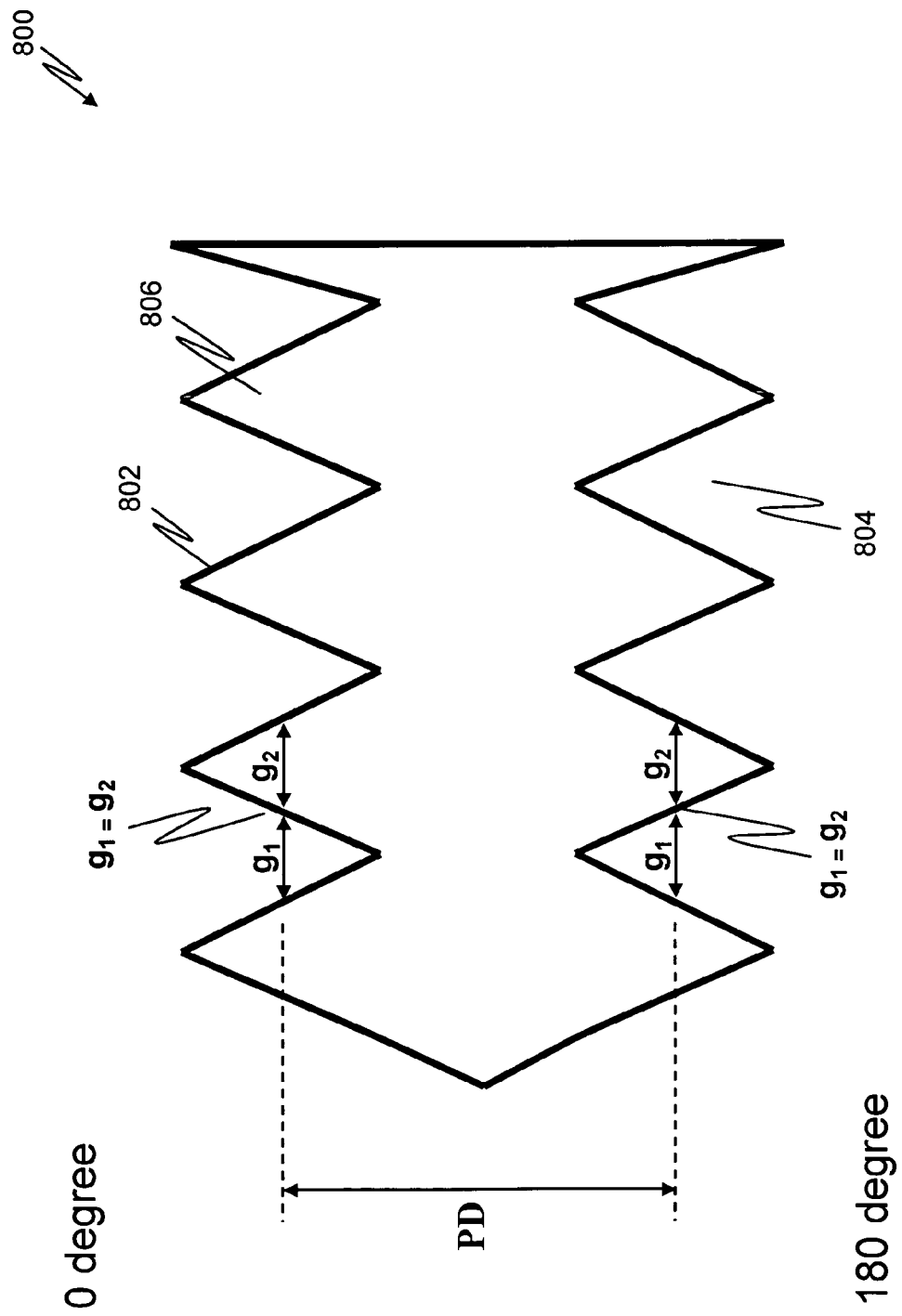
FIG. 24 shows a side view of a symmetrically threaded component.
Figure 25:
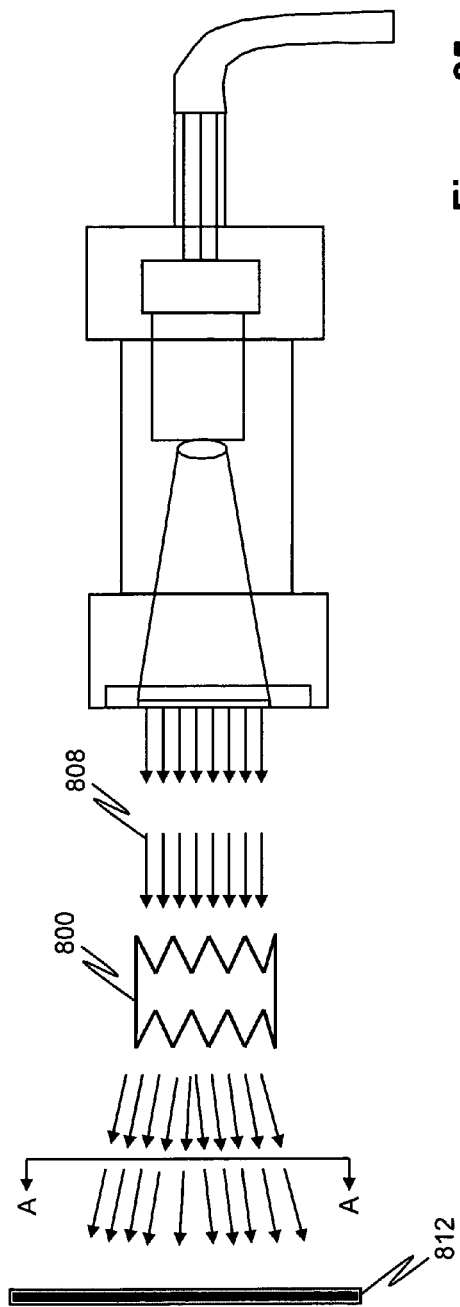
FIG. 25 shows a side view of a silhouette being projected onto a sensing device of the component inspection system of FIG. 1 generated by a collimated light beam incident upon the symmetrically threaded component of FIG. 24.
Figure 26:
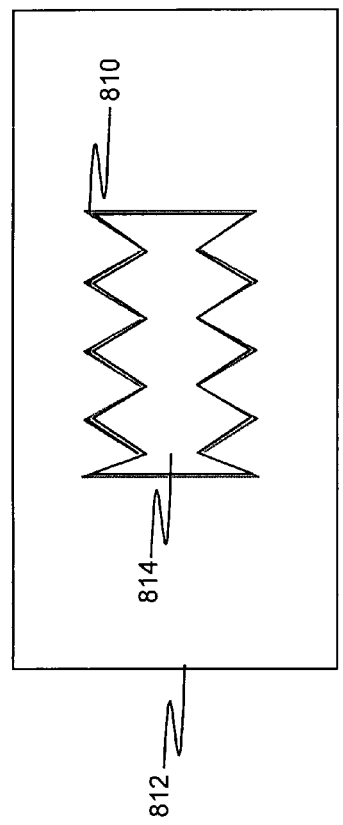
FIG. 26 shows a front view of a sensing device of the component inspection system of FIG. 1 with a silhouette of the symmetrically threaded component of FIG. 24.

In an additional embodiment, the determination of the Pitch Diameter (PD) may include a Correction Factor (CF) to adjust for any aberrations that may be present in the silhouette image data. Referring to FIG. 24, a symmetrically threaded object 800 is shown having a plurality of threads 802. The Pitch Diameter (PD) for the threaded object 800 having thread grooves 804 and thread ridges 806 may be described simply as the distance between a point on the 0° side of the object and the 180° of the object where the width of the thread ridge, $g_1$, and the thread groove; $g_2$, are equal. However referring to FIG. 25 and FIG. 26, as the collimated light beam 808 falls incident upon the object 800, a shadow image 810 may be created and may fall incident upon the sensing device 812 along with the silhouette image 814. As such, the silhouette image data generated by the sensing device 812 may include data responsive to the shadow image 810 and as such, the physical characteristics of the object 800, such as the Pitch Diameter (PD) may be skewed and inaccurate.

In accordance with another embodiment of the invention the inspection system is not limited to a collimated light source and may include any type of electromagnetic radiation source suitable to the desired end purpose which emits energy all along the electromagnetic spectrum, such as non-Laser collimated light, Laser, MASER, electron beam, X-Ray, Microwave, etc. It is contemplated that operation of the inspection system using various other frequencies of EM radiation would be similar to that of collimated light. For example, referring again to FIG. 25 the electromagnetic radiation 800 emitted from the source directly contacts or 'baths' the object 800 causing a 'shadow' representation 810 (having a sillouette 'image') of the object to be created. The 'shadow' representation 810 of the object may then be directly incident upon the sensing device 812 along with the silhouette image 814. As such, the silhouette image data generated by the sensing device 812 may include data responsive to the 'shadow' representation 810 and as such, the physical characteristics of the object 800, such as the Pitch Diameter (PD) may be determined.

To compensate for any aberrations of the shadow image 810 within the silhouette image data, a Correction Factor (CF) may be generated and applied to the process for determining the Pitch Diameter (PD). As such, the Pitch Diameter (PD) may be represented by the equation:

$$PD_{Final}=PD_{Observed}-CF,$$

wherein $PD_{Final}$ is the Pitch Diameter (PD) adjusted for or any aberrations, $PD_{Observed}$ is the Pitch Diameter (PD) as measured and containing any aberrations and CF is the Correction Factor (CF) representing any aberrations.

Figure 27:
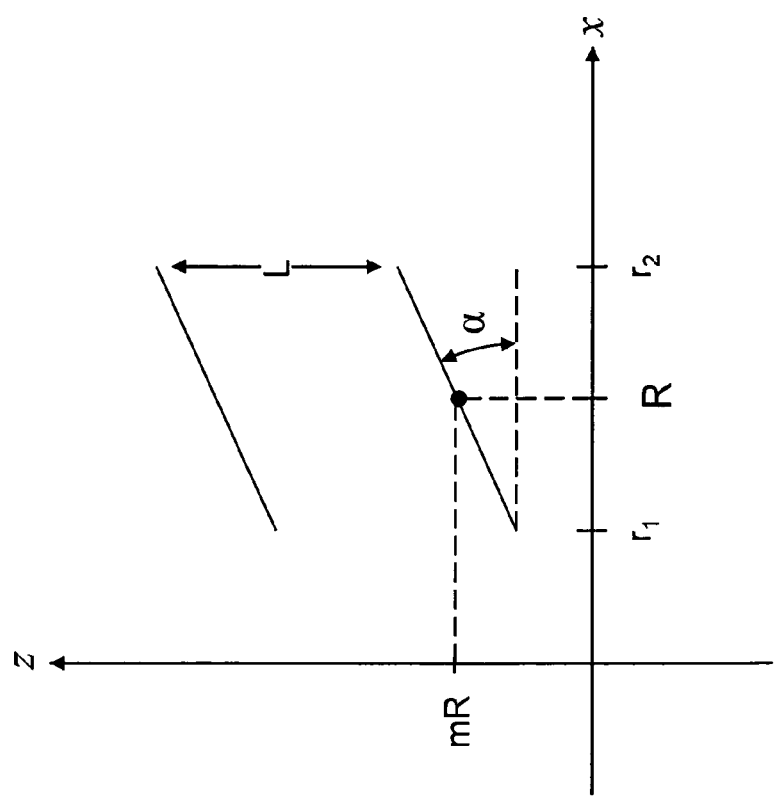
FIG. 27 is a graph of the x-z plane showing a parametric representation of the embedding of the flank of a symmetrically threaded component onto the x-z plane.

For example, one embodiment for compensating for any aberrations includes generating a Correction Factor (CF) responsive to the shadow image and subtracting the Correction Factor (CF) from the silhouette image data generated by the sensing device, wherein the Correction Factor (CF) may be determined by parametrically representing one flank of a thread (i.e. the rear side of a thread ridge) in 3-D space having an x-axis, a y-axis and a z-axis as an embedding of a strip into a 2-D space having only the x-axis and the z-axis. Referring to FIG. 27, for objects or components having symmetrical threads, using only two variables (r, t), a first point, $r_1$, representing the minor diameter of the thread on the x-z axis, and a second point, $r_2$, representing the major diameter of the thread on the x-z axis, is shown in the x-z plane connected via a straight line, $K_{x-z}$, which is drawn between the two points $r_1$ and $r_2$. The variable R is the 2-D representation of the Pitch Diameter (PD) in the x-z plane and t is the flank angle which may be represented as the angle between the line $K_{x-z}$ drawn between the two points, $r_1$ and $r_2$, in the x-z plane and the projection $K_{x-y}$ of the line $K_{x-z}$ onto the x-y plane. Additionally, the variable $L_{x-z}$ is the lead angle of the thread and the variable m is the tangent of the flank angle, t. The variable r is a point on the x-z plane which represents the distance between the z-axis and a point on the line $K_{x-z}$ and thus may range from half of the minor diameter to half of the major diameter. As such, we can parameterize the above relationships using the following equations:

$$x=r\cos(t),$$

$$y=r\sin(t), \text{ and}$$

$$z=mr+Lt/2n.$$

This embedding can then be projected onto the x-z plane by using the equations:

$$x=r\cos(t), \text{ and}$$

$$z=mr+Lt/2n,$$

to obtain the determinant of the Jacobian matrix, wherein the Jacobian matrix is defined by:

$$J(x1 \ldots xn) = \begin{bmatrix} \frac{\partial z1}{\partial x1} & \cdots & \frac{\partial z1}{\partial xn} \\ \vdots & \ddots & \vdots \\ \frac{\partial zn}{\partial x1} & \cdots & \frac{\partial zn}{\partial xn} \end{bmatrix}.$$

As is well known, the Jacobian matrix is the matrix of all first-order partial derivatives of a vector-valued function and may be representative of the 'best' linear approximation to a differential function near a given point.

Thus, using the equations as derived hereinabove, $$x = r\cos(t), \text{ and}$$

$$z = mr + Lt/2\pi,$$

the Jacobian matrix $J(x_1 \ldots x_n)$ may be represented as:

$$J(x1 \ldots xn) = \begin{bmatrix} \cos(t) & -r\sin(t) \\ m & L/2\pi \end{bmatrix}.$$

Solving the Jacobian matrix $J(x_1 \ldots x_n)$ to find the set of points of the shadow image (i.e. ribbon) on the x-z plane gives the following:

$$J = ((L/2\pi)\cos(t) + mr\sin(t)) = 0,$$

where, $$r = -(L/(2\pi m \tan(t))).$$

Figure 28:
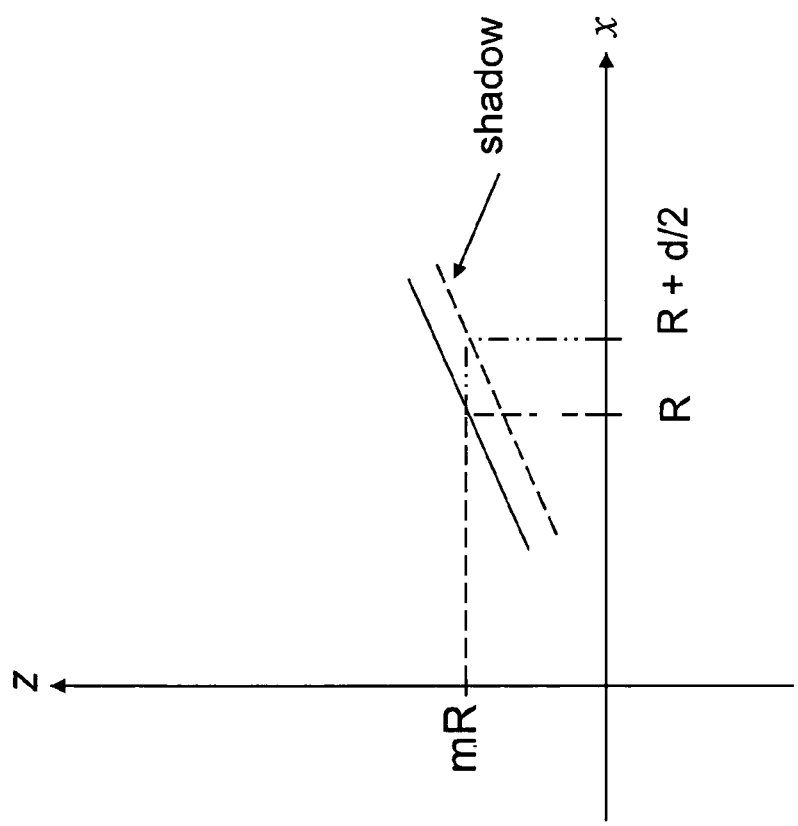
FIG. 28 is a graph of the x-z plane showing a parametric representation of the embedding of the flank of a symmetrically threaded component onto the x-z plane, including an aberration.

Referring to FIG. 28, if the value of R is set to half of the Pitch Diameter (PD) of the thread, the point on the projection of the ribbon that is directly to the "right" of the point where r=R and t=0 may be determined. This is a point on the ribbon that has the same z-coordinate as the Pitch Diameter (PD) point (x,y,z)=(R,0,mR) and thus, it can be seen that at the Pitch Diameter (PD) point (x,y,z), z=mR. Plugging z=mR into the equation for z gives the following:

$$z = mR = mr + \frac{Lt}{(2\pi m)},$$

$$r = R - \frac{Lt}{(2\pi m)},$$

and combining equation (1) with equation (2) gives the following:

$$\frac{-L}{2\pi m \tan(t)} = R - \frac{Lt}{2\pi m},$$

and $$L + (2\pi mR - Lt)\tan(t) = 0,$$

which must be solved for each given value of L, m and R. Having the flank angle, t, these equations may be solved to obtain r, wherein half of the displacement of the Pitch Diameter (PD) is the x-coordinate of the point on the ribbon minus the x-coordinate of the Pitch Diameter (PD) point (x,y,z)=(R, 0,mR) or simply, r cos(t)−R. Thus, it should be appreciated that the Correction Factor (CF) may be assumed to be twice this amount and may be given by the equation:

$$CF = 2(r\cos(t) - R).$$

Thus, the Pitch Diameter for a symmetrically threaded object adjusted for any aberrations, $PD_{Final}$, may be determined by applying the Correction Factor (CF) above into equation (1) to give the following equation:

$$PD_{Final} = PD_{Observed} - 2(r\cos(t) - R),$$

In a similar fashion, for objects or components having asymmetrical threads, such as buttresses, the methodology applied hereinabove may be used for both flanks (due to the asymmetry the calculations should be conducted for each flank). As such, a simple geometric argument using the above approach for both flanks may combine the two results in a kind of weighted average to give:

$$CF = \frac{(d1\tan(a1) + d2\tan(a2))}{(\tan(a1) + \tan(a2))},$$

wherein d1 and d2 are the shadow corrections for the two flank angles treated separately as symmetrical threads and a1 and a2 are the respective flank angles. Given the above, the Pitch Diameter for an asymmetrically threaded object adjusted for any aberrations, $PD_{Final}$, may be determined by applying the Correction Factor (CF) above into equation (1) to give the following equation:

$$PD_{Final} = PD_{Observed} - \frac{(d1\tan(a1) + d2\tan(a2))}{(\tan(a1) + \tan(a2))}.$$

Figure 29:
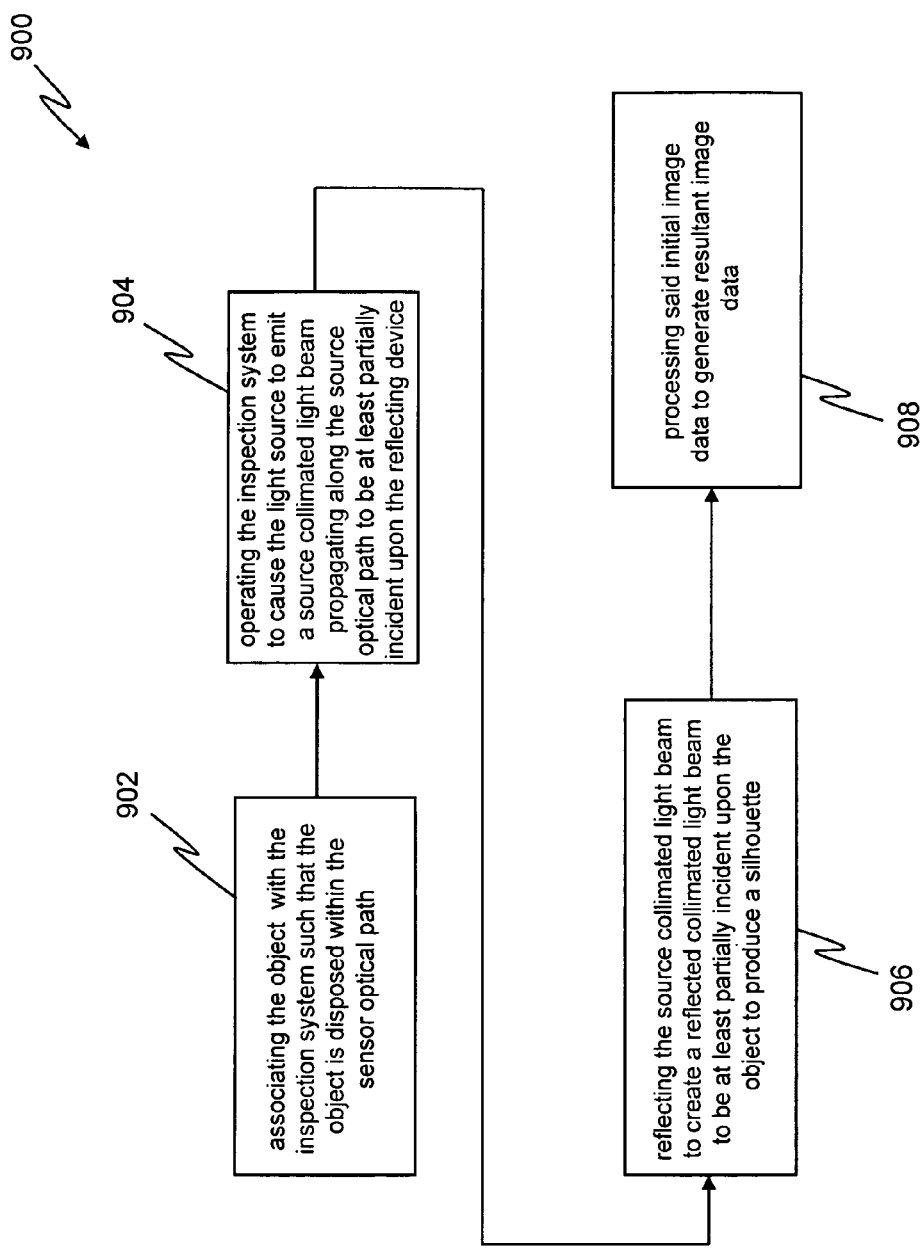
FIG. 29 is a block diagram illustrating a method for measuring the physical characteristics of a component using the component inspection system of FIG. 1.

Referring to FIG. 29, a block diagram illustrating a method 900 for measuring the physical characteristics of a component using an inspection system is shown and includes associating an object with the inspection system 100 such that the object is disposed within the retention mount, as shown in operational block 902. The inspection system is operated to cause the light source to emit a source collimated light beam which propagates along the source optical path, as shown in operational block 904. As the source collimated light beam propagates along the source optical path the source collimated light beam is at least partially incident upon the reflecting device to generate a reflected collimated light beam that propagates along the sensor optical path to be at least partially incident upon the object, as shown in operational block 906. This creates a silhouette of the object, wherein at least a portion of the silhouette is incident upon the sensing device which in response generates initial image data. This initial image data is processed to generate resultant image data responsive to at least one of a plurality of physical characteristics of the object, as shown in operational block 908, wherein the initial image data is processed responsive to at least one predetermined algorithm to correct for any aberrations in the initial image data. As discussed hereinabove, the predetermined algorithm may be responsive to the type of object being inspected. For example, if the object is a threaded object having symmetrical threads, then the predetermined algorithm may be at least partially responsive to the equation:

$$CF = 2(r\cos(t) - R),$$

However, if the object is a threaded object having asymmetrical threads, then the predetermined algorithm may be at least partially responsive to the equation:

$$CF = \frac{(d1\tan(a1) + d2\tan(a2))}{(\tan(a1) + \tan(a2))}.$$

Figure 30:
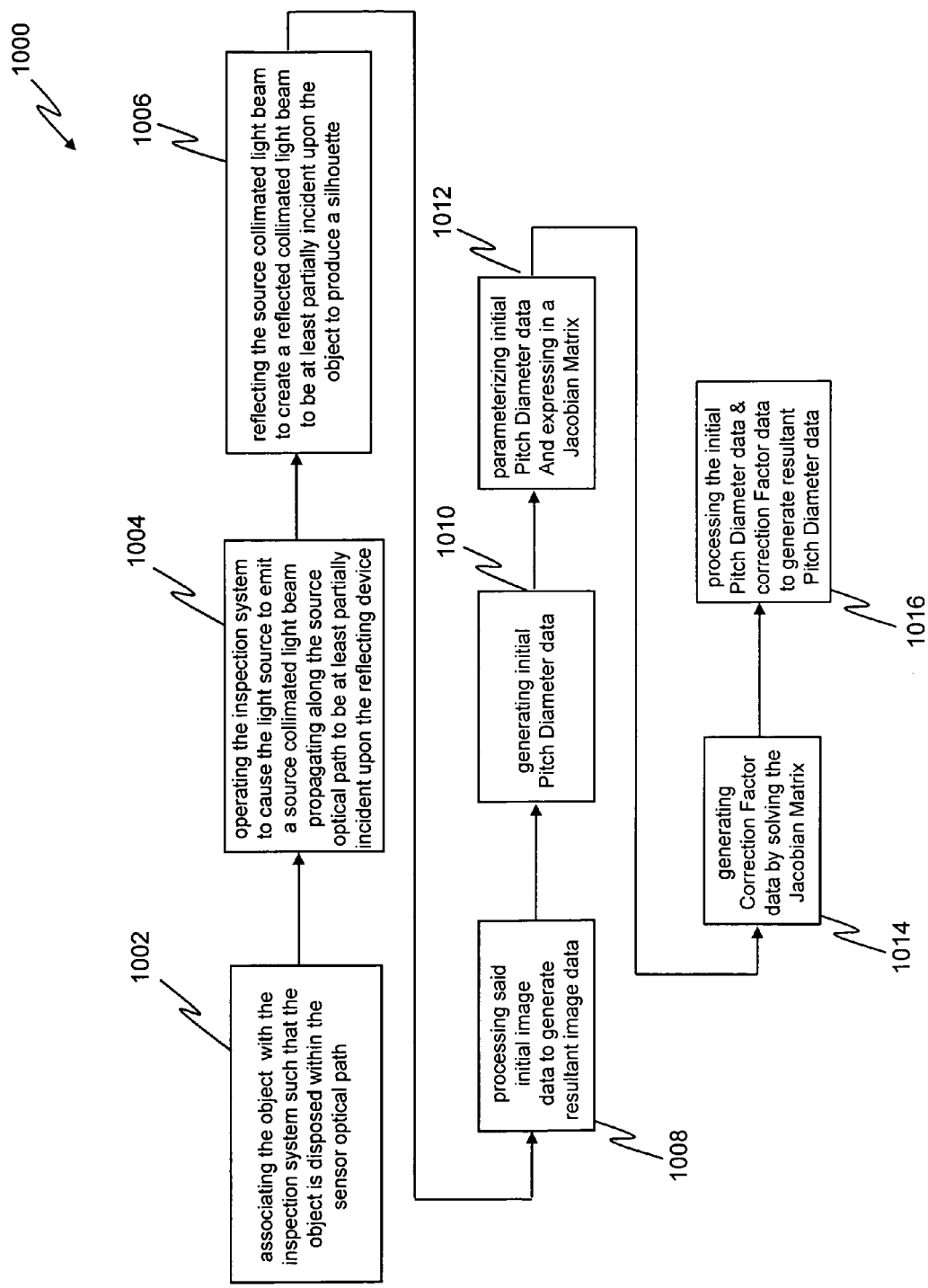
FIG. 30 is a block diagram illustrating a method for correcting aberrations in a component silhouette generated by the component inspection system of FIG. 1.

Referring to FIG. 30, a block diagram illustrating a method 1000 for correcting aberrations in a component silhouette generated by inspection system 100 is shown and includes associating the object 800 with the inspection system 100, as shown in operational block 1002, and operating the inspection system 100 to cause the light source to emit a source light beam that propagates along the source optical path to at least partially incident upon the object 800, as shown in operational block 1004. The source light beam is reflected to create a reflected light beam that propagates alone a sensor optical path to be at least partially incident upon the object 800 to produce a silhouette 814 of the object 800 that is at least partially incident upon the sensing device 812, as shown in operational block 1006, wherein the sensing device 812 generates initial image data responsive to the silhouette and any aberrations in the silhouette. The initial image data is then processed to generate resultant image data, as shown in operational block 1008. This may be accomplished by generating initial Pitch Diameter (PD) data from the initial image data, as shown in operational block 1010. This initial Pitch Diameter (PD) data is then parameterized and expressed in a Jacobian Matrix, $J(x_1 \ldots x_n)$, as shown in operational block 1012, and the Jacobian Matrix, $J(x_1 \ldots x_n)$, is solved responsive to a plurality of physical characteristics of the object to generate Correction Factor (CF) data, as shown in operational block 1014, wherein the plurality of physical characteristics may include at least one of the lead angle, the flank angle, the major diameter and the minor diameter. Once the Correction Factor (CF) data is determined, the initial Pitch Diameter (PD) data is processed responsive to the Correction Factor (CF) data to obtain the resultant Pitch Diameter (PD) data, as shown in operational block 1016.

The multi thread lead, which is responsive to the distance between the lead front and the lead back measurements, may now be determined. Additionally, the lead angle may be determined by an optimistic theoretical line of best fit along the leading flanks of the thread on the 0° side at the truncated location. The trailing angle may be determined by an optimistic theoretical line of best fit along the trailing flanks of the thread on the 0° side at the truncated location. The included angle may then be determined by adding the leading angle and trailing angle.

At this point, the $2^{nd}$ thread 0° side full form measurements are then made, as shown in block 606. This may be accomplished by repositioning positioning stage 128 on the second thread on the 0° side designated as the full form thread location. As discussed above, this designation is dependent upon the thread numbers and thus upon the selection of component 162. Using the silhouette image data, processing device 152 then determines the minor radius, the major radius, the pitch radius and the lead pitch.

The $1^{st}$ full thread 180° side truncated measurements are then conducted, as shown in block 608, and may be accomplished by repositioning positioning stage 128 on the first thread on the 180° side designated as the truncated thread location. Using the silhouette image data, processing device 152 then determines the minor radius, the major radius (for set plug only), the pitch radius and the lead pitch.

The $2^{nd}$ thread 180° side full form measurements are then made, as shown in block 610. This may be accomplished by repositioning positioning stage 128 on the second thread on the 180° side designated as the full form thread location. Using the silhouette image data, processing device 152 then determines the major radius, the pitch radius and the lead pitch.

The component values and limits are then updated and the results are displayed to a system operator and/or printed out in certificate form and positioning stage 128 is repositioned to arbor reference knee position 220, as shown in block 612.

Figure 23:
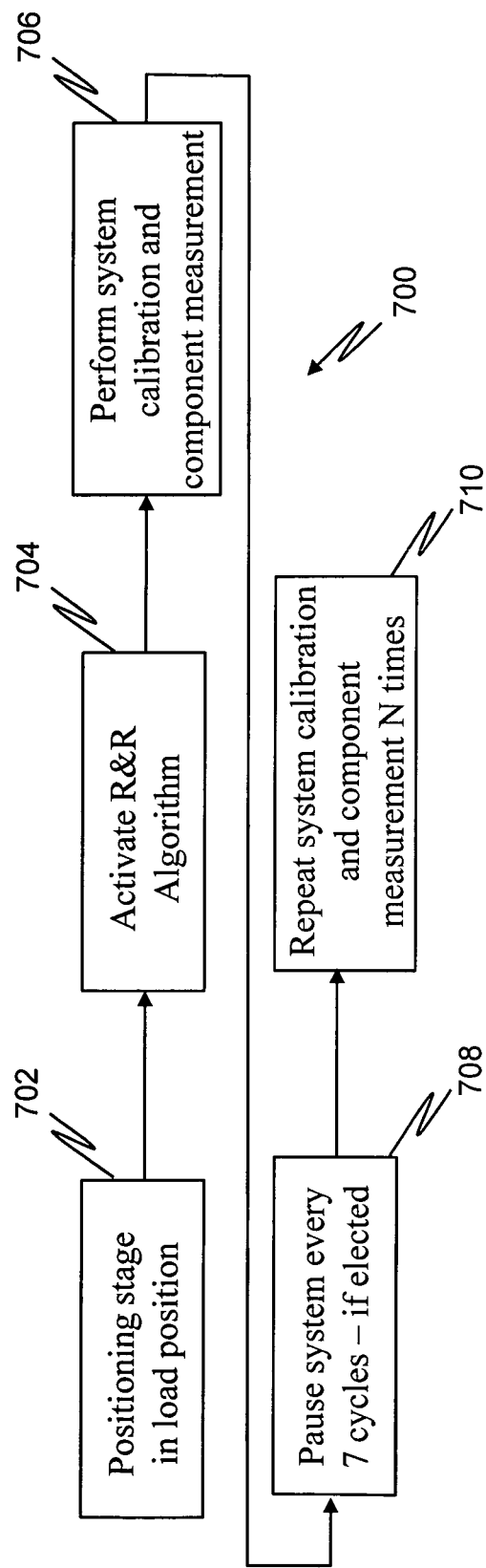
FIG. 23 shows a block diagram illustrating an R&R algorithm.

It is further contemplated that inspection system 100 may perform an R&R (reliability & repeatability) measurement procedure in a manner responsive to a predetermined R&R algorithm 700. Referring to FIG. 23, a block diagram illustrating predetermined R&R algorithm 700 is shown and discussed. Upon initiation of predetermined R&R algorithm 700, positioning stage 128 is positioned into the load position and component 162 is disposed to be retained between first arbor 132 and second arbor 134, as shown in block 702. R&R algorithm 700 is then activated, as shown in block 704. As discussed hereinabove, inspection system 100 then performs predetermined calibration algorithm 500 and predetermined component measurement algorithm 600, as shown in block 706. At this point, once predetermined component measurement algorithm 600 has been completed, the system operator may elect to have inspection system 100 pause every seven cycles for rotation of component 162, as shown in block 708. The measurement cycle may then repeated as many times as desired and the results may then be displayed to the system operator via display device 154 or via a printed certificate or report, as shown in block 710.

It should be appreciated that the measurements described hereinabove for lens distortion analysis, predetermined calibration algorithm 500, predetermined component measurement algorithm 600 and/or R&R algorithm 700 may be accomplished by examining the image data for pixel intensity. This allows inspection system 100 to locate and record known positions on lens 138, first arbor 132, second arbor 134 and/or component 162 as data points. Using these data points, the physical characteristics of lens 138, first arbor 132, second arbor 134 and/or component 162 may be calculated via any method suitable to the desired end purpose, such as geometric/trigonometric relations, estimations and/or predictions.

In accordance with an exemplary embodiment, it is contemplated that multiple measurements may be made at each of the measurement locations in a manner responsive to predetermined component thread specifications. Moreover, the image data may be processed to comprise a plurality of discrete pixel elements. Processing device 142 then conducts each of the measurements by examining each pixel of the plurality of discrete pixel elements to determine the physical characteristics of component 154 as discussed hereinabove. It is further contemplated that image data may be displayed via any display device suitable to the desired end purpose, such as a paper printout, a computer screen, a television, a plasma display and/or a Liquid Crystal Display (LCD). Although the component physical characteristics are determined by processing the image data as discussed hereinabove, the component physical characteristics may be determined by processing the image data using any device and/or method suitable to the desired end purpose. Inspection system 100 may also be operated and/or monitored via a network connection, such as a wireless network (cellular, pager, RF), Local Area Network, Wide Area Network, Ethernet and/or Modem.

It is contemplated that processing device 152 may store image data and measurement results in a data storage device and/or a volatile memory of processing device 152 (e.g. RAM). It should also be noted that image data may be stored in a volatile and/or a non-volatile memory location which may be disposed in any location suitable to the desired end purpose, such as a remote server. In addition, the data storage device may be used to store individual component data and/or group component data which may be specific to a desired purpose, such as data for a specific user, component part and/or a specific end user device, wherein the component data may include a large range of information, such as user specific data and/or component part history data.

In accordance with an exemplary embodiment, inspection system 100 may be a self-calibrating and automated for inspection of multiple components. Moreover, inspection system 100 allows for non-contact measurements which reduce and/or eliminate high inspection costs, operator feel, fatigue, uncertainties and/or error. Inspection system 100 allows for the generation of automatic certificates and information output files. Moreover, inspection system 100 includes built-in repeatability and reliability (R&R) qualification and testing programs and allows for an extremely fast measurement cycle. The measurement and reporting cycles are typically performed in less than two minutes duration. Furthermore, inspection system 100 has an accuracy of about 0.000020 or less. This could never be realized using the current "Attributes" or variables measuring system. Also, inspection system 100 is about 25 times faster than using an "Attributes" or variables measuring system, which will only measure one of the multiple component characteristics required for inspection to satisfy current specifications.

A machine-readable computer program code and/or a medium encoded with a machine-readable computer program code for measuring the characteristics of component 162 using inspection system 100, the code and/or medium including instructions for causing a controller to implement a method including operating inspection system 100, wherein inspection system 100 includes collimated light source 102, a sensing device 104 optically communicated with collimated light source 102 and processing device 152, wherein processing device 152 is communicated with the sensing device 104, disposing component 162 such that component 162 is associated with inspection system 100, positioning component 162 such that component 162 is disposed to partially impede the optical communication between the sensing device 104 and the collimated light source 102, operating the collimated light source 102 such that a collimated light beam is incident upon component 162 to cause a silhouette of component 162 to be received by the sensing device 104, wherein the sensing device 104 generates image data responsive to the silhouette, communicating the image data to processing device 152, processing the image data to determine desired characteristics of component 162 and displaying the characteristics to a user.

In accordance with an exemplary embodiment, the processing of FIGS. 12-13, FIG. 19, FIGS. 22-23 and FIGS. 29-30 may be implemented by a controller disposed internal, external or internally and externally to inspection system 100. In addition, processing of FIGS. 12-13, FIG. 19, FIGS. 22-23 and FIGS. 29-30 may be implemented through a controller operating in response to a computer program. In order to perform the prescribed functions and desired processing, as well as the computations therefore (e.g. execution control algorithm(s), the control processes prescribed herein, and the like), the controller may includes, but not be limited to, a processor(s), computer(s), memory, storage, register(s), timing, interrupt(s), communication interface(s), and input/output signal interface(s), as well as combination comprising at least one of the foregoing.

The invention may be embodied in the form of a computer or controller implemented processes. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. An inspection system, comprising:

an electromagnetic radiation source defining a source optical path, said electromagnetic radiation source being operable to cause electromagnetic radiation to propagate along said source optical path;

a sensing device defining a sensor optical path; a system support structure, a base structure, a bridge structure, an electromagnetic radiation source mounting structure and a sensing device mounting structure;

a positioning device including a positioning device stage, wherein said positioning device stage is movably disposed relative to said positioning device, said sensing device and said electromagnetic radiation source, and wherein said positioning device is non-movably disposed on said base structure; and a retention mount non-movably disposed on said positioning device stage, said retention mount being disposed within said sensor optical path such that when a component is retained within said retention mount, said component blocks at least a portion of said electromagnetic radiation to generate a silhouette, wherein said sensing device generates data responsive to said silhouette.

2. The system of claim 1, further comprising, at least one processing device, wherein said at least one processing device is communicated with said sensing device to receive at least a portion of initial data generated by said sensing device, wherein said processing device processes said at least a portion of said initial data responsive to a Correction Factor (CF).

3. The system of claim 2, wherein said object is at least one of a symmetrically threaded object and an asymmetrically threaded object and wherein said processing device processes said at least a portion of said initial data responsive to a Correction Factor (CF) to determine at least one pitch angle of said object.

4. The system of claim 3, wherein when said object is said symmetrically threaded object said Correction Factor (CF) is at least partially represented by the equation:

$$CF = 2(r\cos(t) - R),$$

wherein CF is the Correction Factor, t is the flank angle, R is a 2-D representation of the Pitch Diameter (PD) in the x-z plane and r is the distance between the z-axis and R.

5. The system of claim 3, wherein when said object is said asymmetrically threaded object said Correction Factor (CF) is at least partially represented by the equation:

$$CF = \frac{(d1\tan(a1) + d2\tan(a2))}{(\tan(a1) + \tan(a2))},$$

wherein CF is the Resultant Correction Factor, d1 is a first partial correction factor for a first flank angle a1 and d2 is a second partial correction factor for a second flank angle a2.

6. The system of claim 5, wherein at least one of said d1 and d2 is at least partially represented by the equation:

$$d = 2(r\cos(a) - R),$$

wherein d is at least one of said first partial correction factor d1 and said second partial correction factor d2, a is at least one of said first flank angle a1 and said second flank angle a2, R is a 2-D representation of the Pitch Diameter (PD) in the x-z plane and r is the distance between the z-axis and R.

7. An inspection system, comprising:
a collimated light source defining a source optical path, said collimated light source being operable to cause a collimated light beam to propagate along said source optical path;
a sensing device defining a sensor optical path; a system support structure, a base structure, a bridge structure, a light source mounting structure and a sensing device mounting structure;
a positioning device including a positioning device stage, wherein said positioning device stage is movably disposed relative to said positioning device, said sensing device and said collimated light source, and wherein said positioning device is non-movably disposed on said base structure; and
a retention mount non-movably disposed on said positioning device stage, said retention mount being disposed within said sensor optical path such that when a component is retained within said retention mount, said component blocks at least a portion of said collimated light beam.

* * * * *